(12) United States Patent
Frohberg

(10) Patent No.: US 8,835,716 B2
(45) Date of Patent: Sep. 16, 2014

(54) PROCESS FOR MODIFYING THE THERMAL AND/OR DIGESTION PROPERTIES OF CORN STARCHES AND CORN FLOURS

(75) Inventor: Claus Frohberg, Kleinmachnow (DE)

(73) Assignee: Bayer Cropscience AG, Monheim am Rhein (DE)

( * ) Notice: Subject to any disclaimer, the term of this patent is extended or adjusted under 35 U.S.C. 154(b) by 169 days.

(21) Appl. No.: 12/521,561

(22) PCT Filed: Dec. 28, 2007

(86) PCT No.: PCT/EP2007/011498
§ 371 (c)(1),
(2), (4) Date: Jun. 26, 2009

(87) PCT Pub. No.: WO2008/080631
PCT Pub. Date: Jul. 10, 2008

(65) Prior Publication Data
US 2010/0317058 A1    Dec. 16, 2010

Related U.S. Application Data

(60) Provisional application No. 61/002,387, filed on Nov. 8, 2007, provisional application No. 60/879,479, filed on Jan. 9, 2007.

(30) Foreign Application Priority Data

Dec. 29, 2006  (EP) .................................. 06090227
Nov. 6, 2007    (EP) .................................. 07075963

(51) Int. Cl.
*A01H 5/00*        (2006.01)
*C12N 15/82*     (2006.01)
*A23L 1/30*        (2006.01)
*C08B 30/00*     (2006.01)
*C12P 19/04*     (2006.01)
*C12N 9/10*       (2006.01)
*C08B 30/04*     (2006.01)

(52) U.S. Cl.
CPC .......... *C08B 30/044* (2013.01); *C12N 15/8245* (2013.01); *C12N 9/1051* (2013.01)
USPC ........ 800/284; 800/320.1; 536/102; 435/101; 435/468; 127/34; 426/648; 514/4.9; 514/5.5

(58) Field of Classification Search
None
See application file for complete search history.

(56) References Cited

U.S. PATENT DOCUMENTS 6,307,125 B1 * 10/2001 Block et al. .................... 800/284
6,734,339 B2 *  5/2004 Block et al. .................... 800/284
7,365,189 B2 *  4/2008 Block et al. .................... 536/102
2009/0106863 A1 *  4/2009 Frohberg et al. .............. 800/298

OTHER PUBLICATIONS

Campbell et al (Cereal Chem. 72(3):281-286.*
Of Campbell et al (Cereal Chem. 72(3):281-286).*
Campbell et al (Cereal Chem. 72(3):281-286).*
Yamamori et al (Australian J. Ag. Res. (2006) 57: 531-53).*
Evans et al (Cereal Chem. (2004) 81(1):31-37).*
Campbell et al (Cereal Chem. (1995) 72(3):281-286.*

* cited by examiner

*Primary Examiner* — David T Fox
*Assistant Examiner* — Lee A Visone
(74) *Attorney, Agent, or Firm* — Hunton & Williams LLP

(57) ABSTRACT

The present invention relates to processes for modifying the thermal and/or digestion properties of corn starches and corn flours.

30 Claims, 2 Drawing Sheets

Figure 1:
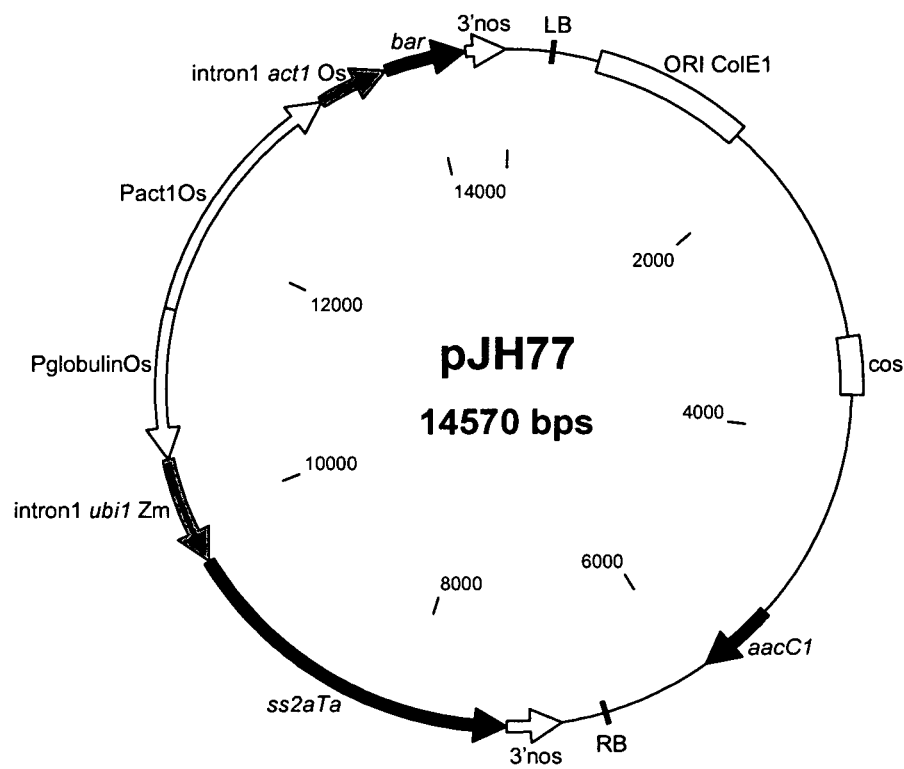

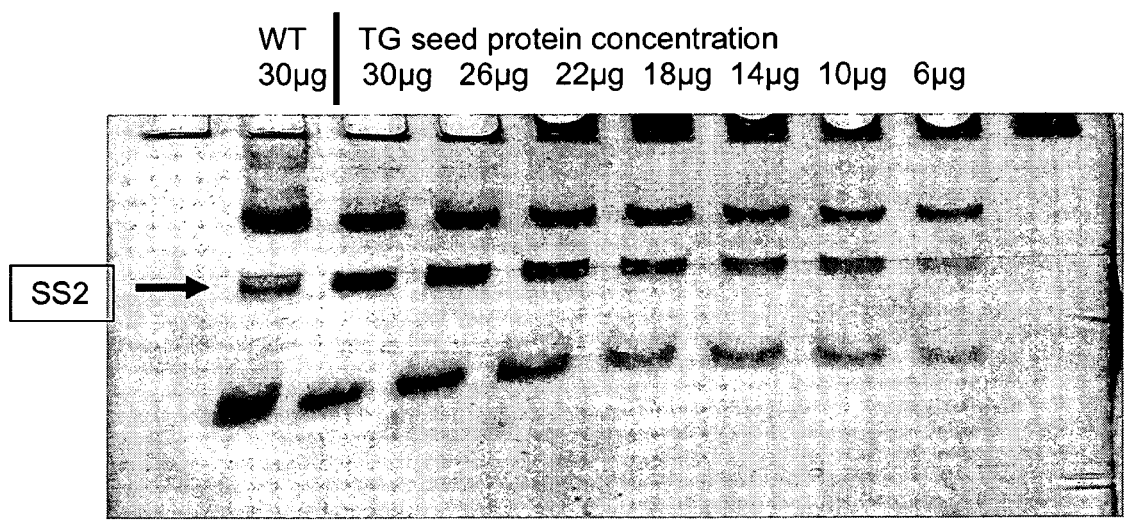
Figure 2: Zymogram

PROCESS FOR MODIFYING THE THERMAL AND/OR DIGESTION PROPERTIES OF CORN STARCHES AND CORN FLOURS

CROSS-REFERENCE TO RELATED APPLICATIONS

This application is the U.S. National Stage filing of International Application No. PCT/EP2007/011498, filed Dec. 28, 2007, which claims priority to European Patent Application No. EP 060 90 227.7, filed Dec. 29, 2006, European Patent Application No. EP 070 75 963.4, filed Nov. 6, 2007, U.S. Provisional Patent Application No. 60/879,479, filed Jan. 9, 2007, and U.S. Provisional Application No. 61/002,387, filed Nov. 8, 2007, the disclosures of which are hereby incorporated in their entirety by reference.

The present invention relates to processes for modifying the thermal and/or digestion properties of corn starches and corn flours.

The polysaccharide starch is made up of chemically uniform basic building blocks, the glucose molecules, but is a complex mixture of differing molecular forms which possess differences with respect to the degree of polymerization and branching, and therefore differ greatly from one another in their physicochemical properties. A differentiation is made between amylose starch, an essentially unbranched polymer of alpha-1,4-glycosidically linked glucose units, and amylopectin starch, a branched polymer in which the branches come about by the occurrence of additional alpha-1,6-glycosidic linkages. A further essential difference between amylose and amylopectin is in the molecular weight. Whereas amylose, depending on origin of the starch, possesses a molecular weight of $5 \times 10^5$-$10^6$ Da, that of amylopectin is between $10^7$ and $10^8$ Da. The two macromolecules can be differentiated by their molecular weight and their different physicochemical properties, which can be made visible most simply by their different iodine binding properties.

Amylose has long been considered a linear polymer consisting of alpha-1,4-glycosidically linked alpha-D-glucose monomers. In more recent studies, however, the presence of a few alpha-1,6-glycosidic branch points has been demonstrated (approximately 0.1%) (Hizukuri and Takagi, Carbohydr. Res. 134, (1984), 1-10; Takeda et al., Carbohydr. Res. 132, (1984), 83-92).

Different methods of determining the amylose content are available which, for one and the same starch, can lead to different numerical/measurement values of amylose content. Some of these methods are based on the iodine-binding capacity of amylose which can be determined potentiometrically (Banks & Greenwood, in W. Banks & C. T. Greenwood, Starch and its components (pp. 51-66), Edinburgh, Edinburgh University Press), amperometrically (Larson et al., Analytical Chemistry 25(5), (1953), 802-804) or spectrophotometrically (Morrison & Laignelet, J. Cereal Sc. 1, (1983), 9-20).

The amylose content can also be determined calorimetrically by means of Differential Scanning Calorimetry (DSC) measurements (Kugimiya & Donovan, Journal of Food Science 46, (1981), 765-770; Sievert & Holm, Starch/Stärke 45(4), (1993), 136-139). In addition, there is the possibility of determining the amylose content via the use of size exclusion chromatography (SEC) of native or debranched starch (Gérard et al., Carbohydrate Polymers 44, (2001), 19-27).

The use of resistant starch (RS) is increasingly growing in importance in the food industry. Starch is chiefly digested in the small intestine by the enzyme alpha-amylase, which hydrolyzes the alpha-1,4-glucosidic bonds of starch to form sugars. In contrast thereto, resistant starch is not digested in the small intestine by alpha-amylases, but passes into the large intestine, where it behaves similarly to dietary fiber. The body obtains energy only to a small extent from the breakdown of RS-containing products. This energy supply solely relates to the oxidative breakdown of resorbed short-chain fatty acids from the large intestine. These short-chain fatty acids are end products of the carbohydrate metabolism of the intestinal microflora. Substrates for the energy metabolism of the intestinal microflora and the large intestine epithelial cells are provided with the intake of RS-containing foods. Large intestine epithelial cells, to maintain their structure and function, have to resort to the luminal supply of short-chain fatty acids and, in particular, butyrate. Resistant starch is apparently a factor for prevention of diverticulosis and large bowel cancer.

A distinction is made between the following types of resistant starch:

$RS_1$ starch physically inaccessible to digestion, for example starch embedded in a protein or fiber matrix. If this is disintegrated physically (for example by chewing) or chemically (for example by breaking down the matrix surrounding it), it can be processed in a usual manner by the digestive juices.

$RS_2$ indigestible intact (granular) native starch grains, for example uncooked potato starch or banana starch, particularly of unripe bananas)

$RS_3$ indigestible retrograded starch which is not granular $RS_4$ indigestible chemically modified starch, for example by crosslinking or esterification (acetylation etc.)

In contrast to RS4, the RS forms 1 to 3 can be made accessible to alpha-amylase breakdown by dissolution in NaOH or dimethyl sulfoxide.

For production of resistant starch, various processes have been described. Most of these processes relate to the production of RS3 starches (EP 564893 A1; EP 688872 A1; EP 846704 A1; U.S. Pat. No. 5,051,271). All of these processes for producing resistant starch comprise the dispersion and gelatinization of starch in large excesses of water, followed by retrogradation with the use of enzymes or acids. They are based on the opinion that resistant starch is formed when the amylose fraction of starch is retrograded after the gelatinization of starch. It is assumed that the linear amylose molecules, after gelatinization, arrange themselves to form tight double-helix configurations bound by hydrogen bonds, so that the alpha-1,4-glucoside bonds are no longer accessible to alpha-amylases. These processes are labor-intensive, time-consuming, and can lead to low yields. Furthermore, the high water content of the products may make expensive drying steps necessary.

For determination of the RS content, use is made of different methods (for example Englyst et al., Eur. J. Clin. Nutr. 46 (Supplement), (1992), S33-S50, Faisant et al., Sci. Aliment. 15, (1995), 83-89; Champ et al., in Advanced Dietary Fibre Technology, B. V. McCleary & Prosky (Eds), Blackwell Science Ltd, Oxford, UK, pp. 106-119; Goni et al., Food Chem. 56, (1996), 445-449; Berry, J. Cereal Sci. 4, (1986), 301-314; McCleary and Monaghan, J. AOAC Int. 85, (2002), 665-675; McCleary et al., J. AOAC Int. 85, (2002), 1103-1111; Approved Methods of the American Association of Cereal Chemists, Tenth Edition, Volume I, (2000), ISBN 1-891127-12-8, AACC Method 32-40) which can lead to differing RS values for a given sample (for example Baghurst et al., Supplement to Food Australia 48(3), (1996), S3-S35). This is especially due to the fact that the four different RS types RS1 to RS4 differ very greatly from one another in their physico-chemical properties, so that they cannot be determined by a single generally valid method (Baghurst et al., Supplement to Food Australia 48(3), (1996), S3-S35). For example, the AOAC/AACC method for determining the content of "dietary fibers" (=DF) provides a grinding step which leads to a destruction of RS1 structures. Some methods are unsuitable for determining the content of RS2 starch, because they provide a step at high temperatures (100° C.) with the use of heat-stable alpha-amylases which inescapably leads to gelatinization of the starches which therefore lose their granular structure and therefore their RS2 structure (Delcour and Eerlingen, Cereal Foods World 41(2), (1996), 85-86).

Granular starches of the RS2 type having a high content of resistant starch are found, especially, in native, uncooked wild type potato starches which, according to the method of determination, have an RS content of 74-85% by weight (Faisant et al., Sciences des Aliments 15, (1995), 83-89; Evans and Thompson, Cereal Chemistry 81(1), (2004), 31-37). Previously known granular corn starches having a high RS fraction are distinguished by a high amylose content (>40% by weight). For native corn starches, that is to say granular corn starches, having a high amylose content, which are synthesized in various corn plants of the genotype amylose extender ("ae"), using the method of determining RS of Englyst et al. (Europ. J. of Clinical Nutrition 46 (Suppl. 2), (1992), pages 33-50), RS values of about 40-70% by weight were determined (Evans and Thompson, Cereal Chemistry 81(1), (2004), 31-37). The RS contents determined by Faisant et al. using two other methods of determining RS, for native, that is to say granular, amylomaize starch of the type Hylon VII (identical to ae VII which was investigated by Evans and Thompson) are, at approximately 54% by weight and 67% by weight, in this range which is also confirmed by an interlaboratory study which, using different methods of determination of RS, gives RS values for native amylomaize starch between about 50 and 72% by weight (McCleary and Monaghan, J. AOAC Int. 85, (2002), 665-675). Such granular amylomaize starches from amylose extender (ae) mutants have, for certain product groups, the disadvantage of poor processing properties, because these starches scarcely gelatinize, and have a low solubility and low swelling capacity. For applications in which only gelatinized starches are usable, or which require soluble starches or starches having swelling capacity, the amylomaize starches are therefore either not suitable at all or they must be additionally chemically modified in order to meet these requirements, which is time-consuming and costly (Senti and Russell, Tappi Vol. 43, No. 4, (April 1960), 343-349; Z. Luo et al., Starch/Stärke 58, (2006), 468-474).

In contrast thereto, conventional granular corn starches which originate from wild type corn plants which do not have amylose extender genotype are distinguished by an amylose content of approximately 24-29% by weight and an RS content which is about 24% by weight (determined according to the method of Englyst et al., see above).

Corn plants having the waxy genotype (also designated "wx") synthesize a granular corn starch which essentially consists of amylopectin. The RS content of this waxy corn starch is about 5% by weight (Evans and Thompson, Cereal Chemistry 81(1), (2004), 31-37).

Owing to the low fraction of resistant starch, therefore neither the granular corn starches from wild type corn plants nor those from waxy corn plants are suitable for use as (prebiotic) additive in the food industry. Other corn mutants which, compared with wild type corn plants, produce a starch or flours having an increased fraction of resistant starch are not currently known. Other processes for increasing in vivo the RS fraction in corn starches are likewise unknown.

In addition to resistant starches (RS), increasingly, also, starches having a high fraction of slowly digestible starch (=SDS) and/or starches having a low fraction of rapidly digestible starch (RDS) are being demanded in food preparation. This is because there is the suspicion that the increasing consumption of foods having a high glycemic loading, such as, for example, in the case of conventional starchy foods having a relatively high RDS fraction, and the resultant insulin secretion, is a risk factor in the occurrence of diseases such as hypertension, overweight, heart disorders and diabetes type II. Foods having a high RDS fraction generally have a high glycemic index (=GI) (Englyst et al., British Journal of Nutrition, 75, 327-337).

The rapid release of relatively large amounts of glucose which may be observed on digestion of conventional starches and absorption thereof via the small bowel epithelium leads to an abrupt increase in the blood sugar level and to a secretion of insulin (insulin response). If the content of SDS is increased and/or the content of RDS of a starch is decreased, this leads to a prolonged release of glucose from the starch, to an altered insulin response and thus finally to a decrease in the risk of the abovementioned diseases.

The use of starches having a high fraction of SDS and/or low fraction of RDS appears desirable in such foods in which continuous release of glucose is sought, such as, for example, in the case of athletes' food for endurance sports or for dietetic food for reducing the feeling of hunger.

It is therefore an object of the present invention to provide processes by which the percentage weight fraction of resistant starch (RS) in corn starch/corn flour can be increased and/or the percentage weight fraction of rapidly digestible starch (RDS) in corn starch/corn flour can be reduced compared with corn starch/corn flour of corresponding wild type corn plants and/or the percentage weight fraction of slowly digestible starch (SDS) in corn starch/corn flour can be increased compared with corresponding corn starches/corn flours of corn amylose extender (ae) plants.

This object is achieved by the embodiments described in the claims.

The present invention therefore relates to a process for producing resistant corn starch in which the percentage weight fraction of resistant starch (RS) in corn starch is increased which comprises expressing a heterologous starch synthase II in a corn plant that has an amylose content between 15% by weight and 40% by weight, preferably between 18% by weight and 35% by weight, and particularly preferably between 20% by weight and 30% by weight, and subsequently extracting the corn starch.

In a particularly preferred embodiment of the process of the invention, the increase of the percentage weight fraction of resistant starch (RS) in corn starch relates to the increase compared with corresponding corn starches from wild type corn plants.

In a further preferred embodiment of the process of the invention, the increase of the percentage weight fraction of resistant starch (RS) in corn starch relates to granular corn starch.

Processes for determining the amylose content are known to those skilled in the art. In the context of the present invention, the amylose content is taken to mean the apparent amylose content. The amylose content is preferably determined by the method described hereinbelow "determination of the apparent amylose content".

The present invention further relates to a process for increasing the percentage weight fraction of resistant starch (RS) in corn starch which comprises expressing a heterologous starch synthase II in a corn plant which has an amylose content between 15% by weight and 40% by weight, preferably between 18% by weight and 35% by weight, and particularly preferably between 20% by weight and 30% by weight.

In a further embodiment of the process of the invention for increasing the percentage weight fraction of resistant starch (RS) in corn starch, the corn starch which is modified by expressing the heterologous starch synthase II in a corn plant is extracted from the corn plant.

In a further embodiment of the process according to the invention, the percentage weight fraction of resistant starch (RS) is increased by at least 10%, preferably by 100%-500%, and particularly preferably by 350%-450%, compared with corn starches from corresponding corn plants, preferably wild type corn plants that do not express a heterologous starch synthase II.

In the context of the present invention, the percentage weight fraction of resistant starch RS, RDS and SDS is preferably determined via the method of Englyst et al. ((Europ. J. of Clinical Nutrition 46 (Suppl. 2), (1992), S 33-50, see, in particular, the following sections from Englyst et al., pages S35-S36: "Reagents, Apparatus, Spectrophotometer"; pages S36-S37, paragraph "Measurement of free glucose (FG)"; page S38, paragraph "Measurement of RDS and SDS"), most preferably the RS, RDS and SDS content is determined by the laboratory scale method described below in the method section "13) Determination of the resistant starch fraction (digestibility)".

The resistant starch fraction (RS) of starch is designated the fraction of the starch sample (dry weight) which is not released as glucose after 2 hours. It is therefore given by the following formula:

RS starch in %=100%−100%×(glucose released after 2 h in mg/dry weight of starch in mg)

In a further embodiment, the present invention relates to a process for producing resistant corn starch in which the percentage weight fraction of rapidly digestible starch (RDS) in corn starch is decreased which comprises expressing a heterologous starch synthase II in a corn plant that has an amylose content between 15% by weight and 40% by weight, preferably between 18% by weight and 35% by weight, and particularly preferably between 20% by weight and 30% by weight, and subsequently extracting the starch.

In a particularly preferred embodiment of the process of the invention, the reduction of the percentage weight fraction of RDS in corn starch relates to the reduction compared with corresponding corn starches of wild type corn plants.

In a particularly preferred embodiment of the process of the invention, the reduction of the percentage weight fraction of RDS in corn starch relates to granular corn starch.

The present invention further relates to a process for decreasing the percentage weight fraction of rapidly digestible starch (RDS) in corn starch, which comprises expressing a heterologous starch synthase II in a corn plant that has an amylose content between 15% by weight and 40% by weight, preferably between 18% by weight and 35% by weight, and particularly preferably between 20% by weight and 30% by weight.

In a further embodiment of the process of the invention for decreasing the percentage weight fraction of rapidly digestible starch (RDS) in corn starch, the corn starch that is modified by expressing the heterologous starch synthase II in a corn plant is extracted from the corn plant.

In a further embodiment of the invention, the percentage weight fraction of rapidly digestible starch (RDS) is decreased by at least 10%, preferably by 15%-50%, particularly preferably by 17%-30%, compared with corn starches from corresponding corn plants, preferably wild type corn plants, that do not express a heterologous starch synthase II.

In a further embodiment of the invention, the percentage weight fraction of rapidly digestible starch (RDS) is reduced by at least 10%, preferably by 15%-75%, particularly preferably by 35%-70%, compared with corn starches from corresponding corn plants, preferably wild type corn plants that do not express a heterologous starch synthase II.

In a further embodiment of the invention, the percentage weight fraction of rapidly digestible starch (RDS) is increased by at least 10%, preferably by 10%-170%, particularly preferably by 10%-100%, compared with corresponding corn starches from amylose-extender (ae) corn plants (such as, for example, Hylon®7).

The present invention further relates to a process for producing resistant corn starch, in which the percentage weight fraction of slowly digestible starch (SDS) in corn starch is increased by expressing a heterologous starch synthase II in a corn plant that has an amylose content between 15% by weight and 40% by weight, preferably between 18% by weight and 35% by weight, and particularly preferably between 20% by weight and 30% by weight, and subsequently extracting the corn starch.

In a particularly preferred embodiment of the process according to the invention, the increase of the percentage weight fraction of slowly digestible starch (SDS) in corn starch relates to the increase compared with the corresponding corn starches of amylose-extender (ae) corn plants (such as, for example, Hylon®7).

In a further preferred embodiment of the process according to the invention, the increase of the percentage weight fraction of slowly digestible starch (SDS) in corn starch relates to granular corn starch.

The present invention further relates to a process for increasing the percentage weight fraction of slowly digestible starch (SDS) in corn starch, which comprises expressing a heterologous starch synthase II in a corn plant that has an amylose content between 15% by weight and 40% by weight, preferably between 18% by weight and 35% by weight, and particularly preferably between 20% by weight and 30% by weight.

In a further embodiment of the process according to the invention for increasing the percentage weight fraction of slowly digestible starch (SDS) in corn starch, the corn starch which is modified by expression of the heterologous starch synthase II in a corn plant is extracted from the corn plant.

In a further embodiment, the percentage weight fraction of slowly digestible starch (SDS) is increased by at least 200%, preferably by 220%-400%, particularly preferably by 240%-300%, compared with corresponding corn starches from amylose-extender (ae) corn plants (such as, for example, Hylon®7) and/or reduced by at least 5% compared with corresponding corn starches from wild type corn plants, preferably by 7%-40%, particularly preferably by 10%-30%.

In a particularly preferred embodiment of the process according to the invention, the increase of the percentage weight fraction of SDS in corn starch relates to the increase compared with corresponding corn starches from amylose extender (ae) corn plants.

In a further preferred embodiment of the process according to the invention, the percentage weight fraction of rapidly digestible starch (RDS) is decreased by at least 10%, preferably by 15%-75%, particularly preferably by 35%-70%, compared with corn starch from corresponding corn plants, preferably wild type corn plants, that do not express a heterologous starch synthase II, and the percentage weight fraction of slowly digestible starch (SDS) is increased by at least 200%, preferably by 220%-400%, particularly preferably by 240%-300%, compared with corresponding corn starches from amylose-extender (ae) corn plants.

The process according to the invention therefore has the advantage that, in addition to a reduced fraction of RDS compared with wild type corn starches, at the same time it is accompanied by an increased fraction of SDS compared with corn starches from amylose extender mutants. The advantages associated with this increase of the SDS fraction of starch such as, for example, a retardation of glucose release (for example athletes' food) and a prolonged feeling of saturation (for example weight management), are therefore coupled with the advantages which are due to the reduced RDS fraction of the starch (for example reduced glycemic response).

The expression amylose extender (ae) mutants, in the context of the present invention, is taken to mean corn plants (plant cells) that have a mutation of the gene of the starch-branching enzyme IIb from corn (abbreviation "BE IIb" or "SBE IIb"), which is also termed the amylose extender gene, wherein this mutation leads to a reduction of the SBE IIb enzyme activity in the endosperm of these corn plants compared with BE IIb activity in the endosperm of wild type corn plants.

This mutation of BE IIb in corn plants (plant cells) can lead to SBE IIb activity no longer being detectable (for example Fisher et al., Plant Physiol. 110 (1996), 611-619, in particular FIG. 4; Hedman and Boyer, Biochemical Genetics 21 (11/12), (1983), 1217-1222, in particular table 1). A BE IIb protein from corn, in the context of the present invention, is taken to mean a branching enzyme of isoform IIb which is encoded by what is termed the amylose extender gene (Kim et al., Plant Molecular Biology 38, (1998), 945-956). The branching enzyme (=BE) of the isoform IIb ($\alpha$-1,4-glucan: $\alpha$-1,4-glucan 6-glycosyltransferase; E.C. 2.4.1.18) catalyzes a transglycosylation reaction in which $\alpha$-1,4-links of an $\alpha$-1,4-glucan donor are hydrolyzed and the $\alpha$-1,4-glucan chains released in this process are transferred to an $\alpha$-1,4-glucan acceptor chain and are thereby converted into $\alpha$-1,6-links. In its biochemical properties, the BEIIb protein from corn differs significantly from the BEI protein from corn which are summarized by Fisher et al. (Plant Physiol. 110, (1996), 611-619) in table 1, page 612. For example, the BEI protein branches amylose more rapidly than the BEIIb protein, whereas the BEIIb protein branches amylopectin at a higher rate than does the BEI protein (Guan and Preiss, Plant Physiol. 102, (1993), 1269-1273). The amino acid sequence of the BEIIb protein differs from the BEIIa protein according to Gao et al. (Plant Physiol. 114, (1997), 69-78) especially by a 49 amino acid-long N-terminal extension of the BEIIa protein. The molecular weight of the BEIIa protein determined by means of SDS-PAGE is 89 kD, that of the BEIIb protein somewhat less, that is to say 85 kDa (Fisher et al., Plant Physiol. 110, (1996), 611-619).

An "amylose extender" gene (also "BEIIb" gene) from corn, in the context of the present invention, is taken to mean a gene which encodes a BEIIb protein.

The "amylose extender mutation" can be a dominant mutation of the amylose extender 1 locus which leads to synthesis of a corn starch that has an apparent amylose content increased compared with wild type corn plants (plant cells) that is between 50 and 90% by weight. Preferably, the dominant mutation is the Mu-induced allele Ae1-5180 of the amylose extender 1 locus (Stinard et al., Plant Cell 5, (1993), 1555-1566).

In addition, the "amylose extender mutation" can be corn plants (plant cells) having a homozygotically recessive "amylose extender" genotype that synthesize a corn starch that has an apparent amylose content of approximately 50-90% by weight. The amylose extender 1 (ae1) locus comprises the structural gene that encodes the SBE IIb protein (Hedman and Boyer, Biochemical genetics 20 (5/6), (1982), 483-492).

Amylose extender (ae) corn mutants have been described, for example, by Vineyard and Bear (Maize Genet Coop Newsletter 26: 5 (1952), who describe the reference allele ae1-Ref, and also by Moore and Creech (Genetics 70, (1972), 611-619), Garwood et al. (Cereal Chemistry 53(3), (1976), 355-364) and Hedman and Boyer (Biochemical Genetics 21 (11/12), (1983), 1217-1222).

In the context of the present invention, "the content of rapidly digestible starch RDS" is to be taken to mean the fraction of a corn starch which is released as glucose after 20 minutes in the abovementioned method of Englyst et al. for determination of the RS content. The report in percent by weight relates in this case to the amount of the starch sample used (dry weight). Therefore, in the context of the present invention, the following applies:

RDS in %=100×glucose released after 20 minutes in mg/dry weight of starch in mg.

In the context of the present invention, "the content of slowly digestible starch (SDS)" is taken to mean the fraction of a corn starch which is released in the abovementioned method of Englyst et al. as glucose after 2 hours, minus the glucose released after 20 minutes (RDS). The statement in percent by weight in this case relates to the dry weight of the starch sample. Accordingly, in the context of the present invention:

SDS in %=100%×(glucose released after 2 h in mg/dry weight of starch in mg)minus(glucose released after 20 min in mg/dry weight of starch in mg).

In the context of the present invention, the sum of the content of SDS, the content of RDS, and the content of RS, is 100%.

A further object of the present invention is to provide processes by which the thermal stability of corn starch/corn flour can be increased.

The present invention therefore relates to a process for producing resistant corn starch in which the thermal stability of corn starch is increased which comprises expressing a heterologous starch synthase II in a corn plant that has an amylose content between 15% by weight and 40% by weight, preferably between 18% by weight and 35% by weight, and particularly preferably between 20% by weight and 30% by weight, and subsequently extracting the corn starch.

The present invention further relates to a process for increasing the thermal stability of corn starch, which comprises expressing a heterologous starch synthase II in a corn plant that has an amylose content between 15% by weight and 40% by weight, preferably between 18% by weight and 35% by weight, and particularly preferably between 20% by weight and 30% by weight.

The thermal properties of corn starch/corn flour may be analyzed by differential scanning calorimetry (DSC). These are described as gelatinization temperature with the values for the DSC T-onset (=lowest gelatinization temperature) and also for DSC T-peak (=highest gelatinization temperature).

The expression "increase in thermal stability", in the context of the present invention, is to be taken to mean an increase of the DSC T-onset temperature of the corn starch/corn flour by at least 3° C., by at least 5° C., preferably by 5° C. to 12.5° C., particularly preferably by 7° C. to 10° C., and/or an increase in the DSC T-peak temperature by at least 4° C., preferably by 4° C. to 11° C., particularly preferably by 6° C. to 9° C., compared with corresponding corn plants that do not express a heterologous starch synthase II, preferably in comparison with corresponding wild type corn plants.

In a further preferred embodiment, the "increase in thermal stability" is taken to mean an increase of the DSC T-onset temperature of the corn starch/corn flour by at least 1.5° C., preferably by 2° C. to 7° C., particularly preferably by 3° C. to 5° C., and/or an increase of the DSC T-peak temperature by at least 2° C., preferably by 3° C. to 7° C., particularly preferably by 4° C. to 6° C. compared with the corresponding corn plants which do not express a heterologous starch synthase II, preferably compared with corresponding wild type corn plants.

The expression "DSC T-onset temperature", in the context of the present invention, is to be taken to mean the temperature that represents the start of the phase transition of the starch sample or of the flour sample. It is characterized as the intersection of the extrapolation of the baseline and the tangent to the ascending flank of the peak through the inflection point.

The expression "DSC T-peak temperature", in the context of the present invention, is taken to mean the temperature at which the DSC curve of the starch sample or of the flour sample has reached a maximum, and the first derivative of the curve is zero.

The "DSC T-onset" temperature and also the "DSC T-peak" temperature, in the context of the present invention, are determined by the method described below ("thermal analysis of corn flour/corn starch by means of differential scanning calorimetry (DSC)").

In a further embodiment, the present invention relates to a process for producing resistant starch in which the thermal stability of corn starch is increased and/or the percentage weight fraction of resistant starch (RS) in corn starch is increased and/or the percentage weight fraction of rapidly digestible starch (RDS) in corn starch is decreased, which comprises expressing a heterologous starch synthase II in a corn plant that has an amylose content between 15% by weight and 40% by weight, preferably between 18% by weight and 35% by weight, and particularly preferably between 20% by weight and 30% by weight, and subsequently extracting the corn starch.

In a further embodiment, the present invention relates to a process for increasing the thermal stability of corn starch and/or for increasing the percentage weight fraction of resistant starch (RS) in corn starch and/or for decreasing the percentage weight fraction of rapidly digestible starch (RDS) in corn starch, which comprises expressing a heterologous starch synthase II in a corn plant that has an amylose content between 15% by weight and 40% by weight, preferably between 18% by weight and 35% by weight, and particularly preferably between 20% by weight and 30% by weight.

In a particularly preferred embodiment of all processes according to the invention, the heterologous starch synthase II is expressed in wild type corn plants that have an amylose content between 20% by weight and 30% by weight.

Compared with conventional processes for producing corn starches having an increased thermal stability and/or modified digestion properties using corn mutants (for example ae or ae wx mutants), the starch yield of which can be significantly decreased compared with wild type corn plants, the process according to the invention has the advantage that expressing the heterologous starch synthase II in corn does not have such losses of yield as a consequence.

In a further embodiment of the processes according to the invention, the corn starch modified according to the invention is extracted from reproductive material and/or from starch-storage parts of a corn plant that expresses a heterologous starch synthase II.

Preferably, the processes of the invention also comprise the step of harvesting the cultivated corn plants or the starch-storage plant parts and/or the reproductive material of these corn plants before extraction of the starch. In a further embodiment, the process of the invention also comprises the step of cultivating the corn plants before harvest.

Processes for extracting the starch from plants or from starch-storage parts of corn plants are known to those skilled in the art. In addition, processes for extracting the starch from various starch-storage plants are described, for example in Starch: Chemistry and Technology (editors: Whistler, BeMiller and Paschall (1994), 2nd edition, Academic Press Inc. London Ltd; ISBN 0-12-746270-8; see, for example, chapter XII, pages 412-468: corn and sorghum starches: production; by Watson; Eckhoff et al., Cereal Chem. 73 (1996), 54-57). The extraction of corn starch on an industrial scale is generally achieved by what is termed wet milling. Devices which are customarily used for extracting starch from plant material are separators, decanters, hydrocyclones, spray dryers and fluidized-bed dryers.

The expression "starch-storage parts", in the context of the present invention, is to be taken to mean those parts of a plant in which starch, in contrast to transitory leaf starch, is stored as a deposit for surviving relatively long periods of time. Preferred starch-storage plant parts are corn kernels, particular preference being given to corn kernels containing an endosperm.

Proteins having the activity of a starch synthase II (ADP-glucose-1,4-alpha-D-glucan 4-alpha-D-glucosyltransferase; EC 2.4.1.21) have in their structure a sequence of defined domains. At the N terminus, they have a signal peptide for transport into plastids. In the direction of the N terminus towards the C terminus, there follow an N-terminal region and a catalytic domain. (Li et al., 2003, Funct Integr Genomics 3, 76-85). Further analyses based on amino acid sequence comparisons (http://hits.isb-sib.ch/cgi-bin/PFSCAN) of various proteins having the activity of a starch synthase II found that these proteins have three specific domains. In the amino acid sequence represented under SEQ ID NO 2, the amino acids 322 to 351 are domain 1, the amino acids 423 to 462 are domain 2 and amino acids 641 to 705 are domain 3. Domain 1 is coded by the nucleotides 1190 to 1279, domain 2 by nucleotides 1493 to 1612 and domain 3 by the nucleotides 2147 to 2350 of the nucleic acid sequence represented under SEQ ID NO 1.

In the context of the present invention, the expression "starch synthase II" is taken to mean a protein which catalyzes a glucosylation reaction in which glucose radicals of the substrate ADP-glucose are transferred to alpha-1,4-linked glucan chains, with formation of an alpha-1,4-link (ADP-glucose+{(1,4)-alpha-D-glucosyl}(N)<=>ADP+{(1,4)-alpha-D-glucosyl}(N+1)). The amino acid sequence of starch synthase II exhibits an identity of at least 86%, preferably at least 93%, particularly preferably at least 95%, with amino acids 322 to 351 (domain 1) of the amino acid sequence represented under SEQ ID NO 2 and/or an identity of at least 83%, preferably at least 86%, particularly preferably at least 95%, with amino acids 423 to 462 (domain 2) of the amino acid sequence represented under SEQ ID NO 2 and/or an identity of at least 70%, preferably at least 82%, preferably 86%, particularly preferably 98%, in particular preferably at least 95%, with amino acids 641 to 705 (domain 3) of the amino acid sequence represented under SEQ ID NO 2.

The expression "identity", in the context of the present invention, is to be taken to mean the number of amino acids/nucleotides in agreement (identity) with other proteins/nucleic acids, expressed in percent. Preferably, the identity of a protein having the activity of a starch synthase II is determined by comparison with the amino acid sequence reported under SEQ ID NO 2, or the identity of a nucleic acid molecule encoding a protein having the activity of a starch synthase II is determined by comparison with the nucleic acid sequence reported under SEQ ID NO 1 with other proteins/nucleic acids by computer programs. If sequences which are compared with one another have different lengths, the identity must be determined in such a manner that the number of amino acids/nucleotides which the shorter sequence has in common with the longer sequence determines the percentage fraction of the identity. Preferably, the identity is determined by means of the known and publicly available computer program ClustalW (Thompson et al., Nucleic Acids Research 22 (1994), 4673-4680). ClustalW is publicly available from Julie Thompson (Thompson@EMBL-Heidelberg.DE) and Toby Gibson (Gibson@EMBL-Heidelberg.DE), European Molecular Biology Laboratory, Meyerhofstrasse 1, D 69117 Heidelberg, Germany. ClustalW can likewise be downloaded from various Internet sites, inter alia from the IGBMC (Institut de Génétique et de Biologie Moléculaire et Cellulaire, B.P.163, 67404 Illkirch Cedex, France; ftp://ftp-igbmc.u-strasbg.fr/pub/) and from the EBI (ftp://ftp.ebi.ac.uk/pub/software/) and also from all mirror Internet sites of the EBI (European Bioinformatics Institute, Wellcome Trust Genome Campus, Hinxton, Cambridge CB10 1SD, UK).

Preferably, version 1.8 of the ClustalW computer program is used to determine the identity between proteins described in the context of the present invention and other proteins. In this procedure the following parameters must be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP. Preferably, version 1.8 of the ClustalW computer program is used in order to determine the identity between, for example, the nucleotide sequence of the nucleic acid molecules described in the context of the present invention and the nucleotide sequence of other nucleic acid molecules. In this process the following parameters must be set: KTUPLE=2, TOPDIAGS=4, PAIRGAP=5, DNAMATRIX: IUB, GAPOPEN=10, GAPEXT=5, MAXDIV=40, TRANSITIONS: unweighted.

"A heterologous" starch synthase II, in the context of the present invention, is to be taken to mean a starch synthase II which does not occur naturally in the corn plant (cell), but whose encoding DNA sequence is introduced into the cell, for example, by genetic engineering methods such as, for example, transformation of the cell. In this process the encoding DNA sequence of the heterologous starch synthase II can originate from another corn variety than the transformed corn plant cell and is in this case preferably not under the control of its own promoter. Preferably, the heterologous starch synthase is from a different plant species to the transformed corn plant cell or corn plant or the starch synthase II used is not under the control of its own promoter. Particularly preferably, the encoding DNA sequence of the heterologous starch synthase II originates from a different plant genus from the transformed corn plant cell or corn plant.

The expression "plant genus", in the context of the present invention, is to be taken to mean a hierarchical stage of biological systematics. A genus contains one or more species. One example of a genus is *Triticum* L. (wheat). All species within a genus always have a two-part (binominal) name which, in addition to the genus name, also contains a species epithet. *Triticum aestivum* L. (soft wheat) is accordingly a species of the genus *Triticum*.

Nucleic acid sequences and the amino acid sequences corresponding thereto which exhibit the required identity with domains 1, 2 and 3 and which encode a starch synthase II are known to those skilled in the art and are published, for example, by Gao and Chibbar (Genome 43 (5), (2000), 768-775: starch synthase II from wheat NCBI Acc No. AJ269502.1, AJ269503.1, AJ269504.1) or under Accession No. AF155217.2 (*Triticum aestivum*), AY133249 (*Hordeum vulgare*), Accession No. AY133248 (*Aegilops tauschii*), Accession Nos. XP467757, AAK64284 (*Oryza sativa*), Accession No. AAK81729 (*Oryza sativa*) Accession Nos. AAD13341, AAS77569, Accession No. AAF13168 (*Manihut esculenta*), Accession No. AAP41030 (*Colocasia esculenta*), Accession No. AAS88880 (*Ostraeococcus tauri*), or Accession No. AAC17970 (*Chlamydomonas reinhardii*). Said nucleic acid sequences and amino acid sequences encoding a protein having the activity of a starch synthase II are accessible via NCBI (http://www.ncbi.nlm.nih.gov/entrez/) and are hereby explicitly incorporated into the contents of the present application by naming the references.

In a particularly preferred embodiment, in the context of the present invention, use is made of a starch synthase II of the genus *Triticum*, preferably of the species *Triticum aestivum*. Particular preference is given to starch synthase II having the amino acid sequence reported under SEQ ID NO 2 or the nucleotide sequence reported under SEQ ID NO 1.

In a further embodiment of the process according to the invention, the corn plant (cell) is genetically modified, wherein the genetic modification leads to an increase of the activity of a starch synthase II compared with corresponding wild type corn plant cells or wild type corn plants which are not genetically modified.

The genetic modification in this case can be any genetic modification which leads to an increase in the activity of a starch synthase II compared with corresponding wild type corn plant cells or wild type corn plants which are not genetically modified.

The expression "wild type corn plant cell", in the context of the present invention, means that these are corn plant cells which served as starting material for producing corn plant cells which synthesize the starch of the invention. The expression "wild type corn plant cell", in the context of the present invention, does not comprise corn plant cells of corn mutants of the ae (amylose extender), wx (waxy), du (dull), sh2 (shrunken 2), brittle-1 or brittle-2 genotype or of double or multiple mutants of these genotypes. The expression "wild type corn plant", in the context of the present invention, means that this is a corn plant which served as starting material for producing corn plants which synthesize the starch of the invention. The expression "wild type corn plant", in the context of the present invention, does not comprise corn mutants of the ae (amylose extender), wx (waxy), du (dull), sh2 (shrunken 2), brittle-1 or brittle-2 genotype or of double or multiple mutants of these genotypes.

Preferably, the expression "wild type corn plant" refers to the corn inbred line A188 which is publicly available, for example via the Maize Genetics Cooperation Stock Center (http://maizecoop.cropsci.uiuc.edu/) at the University of Illinois, Urbana/Champaign, USA.

The expression "corresponding", in the context of the present invention, means that, in the comparison of a plurality of items, the items in question which are compared with one another are kept under the same conditions. In the context of the present invention the expression "corresponding", in the context of wild type corn plant cell or wild type corn plant means that the plant cells or plants which are compared with one another have been grown under identical cultivation conditions and that they have an identical (cultivation) age.

The expression "increasing the activity of a starch synthase II", in the context of the present invention, means increasing the expression of endogenous genes which encode proteins having the activity of a starch synthase II and/or preferably increasing the enzymatic activity of proteins having the activity of a starch synthase II in the corn plant (cells).

The increase in expression can be determined, for example, by measuring the amount of transcripts which encode proteins having the activity of a starch synthase II. The determination can proceed, for example, by Northern Blot analysis or RT-PCR.

The amount of the activity of a protein having the activity of a starch synthase II can be determined, for example, as described in the literature (Nishi et al., 2001, Plant Physiology 127, 459-472). A method for determining the amount of activity of a protein having the activity of a starch synthase II, which method is preferred in the context of the present invention, is described hereinbelow ("determination of SSII activity by means of an activity gel").

Preferably, the corn plant (cells) that are modified according to the invention have an enzymatic activity of starch synthase II which is increased by at least 2 times, preferably 3-10 times, particularly preferably 4-6 times, compared with corresponding wild type corn plant cells or wild type corn plants that are not genetically modified.

In a further embodiment of the present invention, the genetic modification is the introduction of at least one foreign nucleic acid molecule into the genome of the plant cell or into the genome of the plant.

In this context, the expression "genetic modification" means the introduction of at least one foreign nucleic acid molecule into the genome of a corn plant (cell), wherein said introduction of this molecule leads to an increase in the activity of a protein having the activity of a starch synthase II.

By introducing a foreign nucleic acid molecule, the corn plant (cells) modified according to the invention are changed in their genetic information. The presence or the expression of at least one foreign nucleic acid molecule leads to a change in phenotype. "Change in phenotype" in this case preferably means a measurable change of one or more functions of the cells. For example, the genetically modified corn plant (cells), on account of the presence or on expression of introduced foreign nucleic acid molecules, exhibit an increase in the activity of a protein having the activity of a starch synthase II and synthesize a starch having an increased thermal stability, an increased RS content and/or a decreased RDS content.

The expression "foreign nucleic acid molecule" is taken to mean, in the context of the present invention, a molecule which either does not occur naturally in corresponding wild type corn plant cells, or which does not occur naturally in wild type corn plant cells in the specific spatial arrangement, or which is localized at a site in the genome of the wild type corn plant cell at which it does not naturally occur. In principle, a foreign nucleic acid molecule can be any desired nucleic acid molecule which, in the plant cell or plant, causes an increase in the activity of a protein having the activity of a starch synthase II.

Preferably, the foreign nucleic acid molecule is a recombinant nucleic acid molecule which consists of various elements, the combination or specific spatial arrangement of which does not occur naturally in plant cells.

The expression "recombinant nucleic acid molecule", in the context of the present invention, is to be taken to mean a nucleic acid molecule which has differing nucleic acid molecules which are not naturally present in a combination as they are present in a recombinant nucleic acid molecule. For instance, the recombinant nucleic acid molecules exhibit, for example, in addition to nucleic acid molecules which encode a protein having the activity of a starch synthase II (for example genomic nucleic acid molecules or cDNAs), additional nucleic acid sequences which are not naturally present in combination with these nucleic acid molecules. The recombinant nucleic acid molecule has, for example, regulatory sequences (for example promoters, termination signals, enhancers), preferably regulatory sequences which are heterologous with respect to the nucleic acid molecule which encodes the starch synthase II. Heterologous in this context means that the regulatory sequence is not the endogenous regulatory sequences of the starch synthase II gene used itself. In addition, preference is given to regulatory sequences which are active in plant tissue.

Suitable promoters are constitutive promoters such as, for example, the promoter of the 35S RNA of Cauliflower Mosaic Virus (Odell et al., 1985, Nature, 313, 810-812), the ubiquitin promoter from corn (Christensen et al., Plant Mol. Biol. 18, (1992), 675-689), the ubiquitin promoter from rice (Liu et al., Plant Science 165, (2003), the rice actin promoter (Zhang, et al., Plant Cell 3:1150-1160, 1991), the Cassaya Vein Mosaic Virus (CVMV) promoter (Verdaguer et. al., Plant Mol. Biol. 31: 1129-1139), the corn histone H3C4 promoter (U.S. Pat. No. 6,750,378) or the Cestrum YLCV promoter (Yellow Leaf Curling Virus; WO 01 73087; Stavolone et al., 2003, Plant Mol. Biol. 53, 703-713).

Particularly preferably these are tissue-specific regulatory sequences which are active in corn tissue, preferably in the endosperm of corn plants. Further endosperm-specific promoters in corn are the promoter des10 kD zein gene from corn (Kirihara et al. (1988) Gene 71: 359-370), the 15 kD zein gene from corn (Hoffmann et al. (1987) EMBO J. 6: 3213-3221; Schernthaner et al. (1988) EMBO J. 7: 1249-1253; Williamson et al. (1988) Plant Physiol. 88: 1002-1007), the 27 kd zein gene from corn (Prat et al. (1987) Gene 52: 51-49; Gallardo et al. (1988) Plant Sci. 54: 211-281), the 19 kD zein gene from corn (Marks et al. (1985) J. Biol. Chem. 260: 16451-16459). The relative transcriptional activities of these promoters in corn are described in Kodrzyck et al., (1989), Plant Cell 1, 105-114).

Other promoters which are conceivable in combination with the present invention are the promoter of the sucrose synthase gene (Yang, N.-S. and Russel, D. (1990) Proc. Natl. Acad Sci 87: 4144-4148), of the waxy gene (Unger et al. (1991) Plant Physiol. 96: 124), of the sh 2 gene (Bhave et al. (1990) Plant Cell 2: 581-588, of the bt 2 gene (Bae et al. (1990) Maydica 35: 317-322). In addition the HMG promoter (also termed wheat glutenin HMWG promoter) from wheat (Colot et al., EMBO J. 6, (1987, 3559-3564; Clarke and Appels, Genome 41, (1998), 865-871), the USP promoter, the phaseolin promoter, promoters of zein genes from corn (Pedersen et al., Cell 29 (1982), 1015-1026; Quatroccio et al., Plant Mol. Biol. 15 (1990), 81-93), the glutelin promoter (Leisy et al., Plant Mol. Biol. 14 (1990), 41-50; Zheng et al., Plant J. 4 (1993), 357-366; Yoshihara et al., FEBS Lett. 383 (1996), 213-218), the globulin promoter (Nakase et al., 1996, Gene 170(2), 223-226) or the prolamine promoter (Qu and Takaiwa, 2004, Plant Biotechnology Journal 2(2), 113-125).

Intron sequences can also be present between the promoter and the coding region. Such intron sequences can lead to stability of expression and to an increased expression in plants (Callis et al., 1987, Genes Devel. 1, 1183-1200; Luehrsen, and Walbot, 1991, Mol. Gen. Genet. 225, 81-93; Rethmeier, et al., 1997; Plant Journal. 12(4):895-899; Rose and Beliakoff, 2000, Plant Physiol. 122 (2), 535-542; Vasil et al., 1989, Plant Physiol. 91, 1575-1579; XU et al., 2003, Science in China Series C Vol. 46 No. 6, 561-569). Suitable intron sequences are, for example, the first intron of the sh1 gene from corn (Maas et al. (1991) Plant. Mol. Biol. 16: 199-207, the first intron of the polyubiquitin gene 1 from corn, the first intron of the EPSPS gene from rice or one of the two first introns of the PAT1 gene from *Arabidopsis*, in addition introns of the Adh-1 or Bz-1 gene from corn (Callis et al. (1987) Genes Dev. 1: 1183-1200), intron 3 of the corn actin gene (Luehrsen, K. R. and Walbot, V. (1991) Mol. Gen. Genet. 225: 81-93) or of the Adh1 intron 6 (Oard et al. (1989) Plant Cell Rep 8: 156-160).

Methods of producing recombinant nuclear acid molecules are known to those skilled in the art and comprise genetic engineering methods such as, for example, binding nucleic acid molecules by ligation, genetic recombination or denovo synthesis of nucleic acid molecules (see, for example, Sambrok et al., Molecular Cloning, A Laboratory Manual, 3rd edition (2001) Cold Spring Harbour Laboratory Press, Cold Spring Harbour, N.Y. ISBN: 0879695773, Ausubel et al., Short Protocols in Molecular Biology, John Wiley & Sons; 5th edition (2002), ISBN: 0471250929).

The expression "genome", in the context of the present invention, is to be taken to mean the totality of the hereditary material present in a plant cell. It is known to those skilled in the art that, in addition to the cell nucleus, hereditary material is also present in other compartments (for example plastids, mitochondria).

In a further embodiment, the present invention relates to a process for producing corn flour in which the percentage weight fraction of resistant starch (RS) is increased in the corn flour, which comprises expressing a heterologous starch synthase II in a corn plant that has an amylose content between 15% by weight and 40% by weight, preferably between 18% by weight and 35% by weight, and particularly preferably between 20% by weight and 30% by weight, and subsequently milling the corn plant or parts of this corn plant that express the heterologous starch synthase II to give corn flour.

The present invention further relates to a process for increasing the percentage weight fraction of resistant starch (RS) in corn flour which comprises expressing a heterologous starch synthase II in a corn plant that has an amylose content between 15% by weight and 40% by weight, preferably between 18% by weight and 35% by weight, and particularly preferably between 20% by weight and 30% by weight.

In a particularly preferred embodiment of the process according to the invention, the increase of the percentage weight fraction of resistant starch (RS) in corn flour relates to the increase compared with corresponding corn flours from wild type corn plants.

In a further embodiment of the process according to the invention for increasing the percentage weight fraction of resistant starch (RS) in corn flour, the corn flour that is modified by the expression of the heterologous starch synthase II in a corn plant is obtained from the corn plant.

In a further embodiment of the invention, the percentage weight fraction of resistant starch (RS) of the corn flour is increased by at least 10%, preferably by 20%-100%, and particularly preferably by 30%-50%, compared with corn flour from corresponding corn plants, preferably wild type corn plants, that do not express a heterologous starch synthase II.

The RS content of the corn flour is determined in the context of the present invention, preferably, via the method of Englyst et al. ((Europ. J. of Clinical Nutrition 46 (Suppl. 2), (1992), S 33-50, see, in particular, the following sections from Englyst et al., pages S35-S36: "Reagents, Apparatus, Spectrophotometer"; pages S36-S37, paragraph "Measurement of free glucose (FG)"; page S38, paragraph "Measurement of RDS and SDS"). The "percentage weight fraction of resistant starch (RS) of the corn flour", in the context of the present invention, is designated the fraction of the weighed-out flour sample (dry weight) which is not released as glucose after 2 hours in the method of Englyst et al. It is therefore given by the following formula:

$$\text{RS flour in \%} = 100\% - 100\% \times (\text{glucose released after 2 h in mg/dry weight of flour in mg})$$

In a further embodiment, the present invention relates to a process for producing corn flour in which the percentage weight fraction of resistant starch (RS) of the starch component in corn flour is increased, by expressing a heterologous starch synthase II in a corn plant that has an amylose content between 15% by weight and 40% by weight, preferably between 18% by weight and 35% by weight, and particularly preferably between 20% by weight and 30% by weight, and subsequently grinding the corn plant, or parts of this corn plant, that expresses the heterologous starch synthase II to give corn flour.

The present invention further relates to a process for increasing the percentage weight fraction of resistant starch (RS) of the starch component in corn flour which comprises expressing a heterologous starch synthase II in a corn plant that has an amylose content between 15% by weight and 40% by weight, preferably between 18% by weight and 35% by weight, and particularly preferably between 20% by weight and 30% by weight.

In a particularly preferred embodiment of the process according to the invention, the increase of the percentage weight fraction of resistant starch (RS) of the starch component in corn flour relates to the increase compared with the starch component of corresponding corn flours of wild type corn plants.

In a further embodiment of the process according to the invention for increasing the percentage weight fraction of resistant starch (RS) of the starch component in corn flour, the corn flour modified by expression of the heterologous starch synthase II in a corn plant is obtained from the corn plant.

In a further embodiment of the invention, the percentage weight fraction of resistant starch (RS) of the starch component of the corn flour is increased by at least 10%, preferably by 20%-100%, and particularly preferably by 30%-50%, compared with corn flour from corresponding corn plants, preferably wild type corn plants, that do not express a heterologous starch synthase II.

The percentage weight fraction of resistant starch (RS) of the starch component of the corn flour, in the context of the present invention, is determined as already described above for corn starches, after the corn starch has been isolated from the corn flour. Methods for isolating corn starch from corn flour are known to those skilled in the art. Preferably, the corn starch is isolated from the corn flour using the method described hereinbelow "extraction of corn starch".

In a further embodiment, the present invention relates to a process for producing corn flour in which the percentage weight fraction of rapidly digestible starch (RDS) in the corn flour is decreased, which comprises expressing a heterologous starch synthase II in a corn plant that has an amylose content between 15% by weight and 40% by weight, preferably between 18% by weight and 35% by weight, and particularly preferably between 20% by weight and 30% by weight, and subsequently milling the corn plant or parts of this corn plant that express the heterologous starch synthase II to give corn flour.

In a particularly preferred embodiment of the process according to the invention, the reduction of the percentage weight fraction of RDS in corn flour relates to the reduction compared with corresponding corn flours of wild type corn plants.

The present invention further relates to a process for decreasing the percentage weight fraction of rapidly digestible starch (RDS) in corn flour, which comprises expressing a heterologous starch synthase II in a corn plant that has an amylose content between 15% by weight and 40% by weight, preferably between 18% by weight and 35% by weight, and particularly preferably between 20% by weight and 30% by weight.

In a further embodiment of the process according to the invention for decreasing the percentage weight fraction of rapidly digestible starch (RDS) in corn flour, the corn flour that is modified by the expression of the heterologous starch synthase II in a corn plant is obtained from the corn plant.

In a further embodiment of the process according to the invention for producing corn flour the percentage weight fraction of rapidly digestible starch (RDS) in the corn flour is decreased by at least 10%, preferably by 15%-50%, particularly preferably by 17%-30%, compared with corn flour from corresponding corn plants, preferably wild type corn plants, which do not express a heterologous starch synthase II.

In the context of the present invention, the "percentage weight fraction of rapidly digestible starch (RDS) in the corn flour" is to be taken to mean the fraction of a corn flour which is released as glucose after 20 minutes in the abovementioned method of Englyst et al. for determining the RS content. The report in percent by weight is based in this case on the dry weight of the flour sample. Accordingly, in the context of the present invention, the following applies:

Rapidly digestible starch in the flour in %=100×glucose released after 20 minutes in mg/dry weight of flour in mg.

In a further embodiment, the present invention relates to a process for producing corn flour in which the percentage weight fraction of rapidly digestible starch (RDS) of the starch component is reduced in the corn flour by expressing a heterologous starch synthase II in a corn plant that has an amylose content between 15% by weight and 40% by weight, preferably between 18% by weight and 35% by weight, and particularly preferably between 20% by weight and 30% by weight, and subsequently grinding the corn plant, or parts of this corn plant, that expresses the heterologous starch synthase II to give corn flour.

In a particularly preferred embodiment of the process according to the invention, the decrease of the percentage weight fraction of RDS of the starch component in the corn flour relates to the decrease compared with the starch component of corresponding corn flours of wild type corn plants.

The present invention further relates to a process for reducing the percentage weight fraction of rapidly digestible starch (RDS) of the starch component in corn flour, which comprises expressing a heterologous starch synthase II in a corn plant that has an amylose content between 15% by weight and 40% by weight, preferably between 18% by weight and 35% by weight, and particularly preferably between 20% by weight and 30% by weight.

In a further embodiment of the process according to the invention for reducing the percentage weight fraction of rapidly digestible starch (RDS) of the starch component in corn flour, the corn flour which is modified by expression of the heterologous starch synthase II in a corn plant is obtained from the corn plant.

In a further embodiment of the process according to the invention for producing corn flour, the percentage weight fraction of rapidly digestible starch (RDS) of the starch component in the corn flour is reduced by at least 10%, preferably by 15%-75%, particularly preferably by 35%-70%, compared with corn starches from corresponding corn plants, preferably wild type corn plants, which do not express a heterologous starch synthase II.

The percentage weight fraction of rapidly digestible starch (RDS) of the starch component in the corn flour, in the context of the present invention, is determined as already described above for corn starches after the corn starch has been isolated from the corn flour. Methods for isolation of corn starch from corn flour are known to those skilled in the art. Preferably, the corn starch is isolated from the corn flour using the method described herein below "extraction of corn starch".

In a further embodiment, the present invention relates to a process for producing corn flour, in which the percentage weight fraction of slowly digestible starch (SDS) of the starch component in the corn flour is increased by expressing a heterologous starch synthase II in a corn plant that has an amylose content between 15% by weight and 40% by weight, preferably between 18% by weight and 35% by weight, and particularly preferably between 20% by weight and 30% by weight, and subsequently grinding the corn plant, or parts of this corn plant, that expresses heterologous starch synthase II to give corn flour.

The present invention further relates to a process for increasing the percentage weight fraction of slowly digestible starch (SDS) of the starch component in corn flour, which comprises expressing a heterologous starch synthase II in a corn plant that has an amylose content between 15% by weight and 40% by weight, preferably between 18% by weight and 35% by weight, and particularly preferably between 20% by weight and 30% by weight.

In a particularly preferred embodiment of the process according to the invention, the increase of the percentage weight fraction of slowly digestible starch (SDS) of the starch component in corn flour relates to the increase compared with the starch component of corresponding corn flours of amylose-extender (ae) corn plants.

In a further embodiment of the process according to the invention for increasing the percentage weight fraction of slowly digestible starch (SDS) of the starch component in corn flour, the corn flour which is modified by expression of the heterologous starch synthase II in a corn plant is obtained from the corn plant.

In a further embodiment of the invention, the percentage weight fraction of slowly digestible starch (SDS) of the starch component of the corn flour is increased by at least 200%, preferably by 220%-400%, particularly preferably by 240%-300%, compared with the starch component of corresponding corn flours of amylose-extender (ae) corn plants and/or reduced by at least 5% compared with corresponding corn starches from wild type corn plants, preferably by 7%-40%, particularly preferably by 10%-30%.

The percentage weight fraction of slowly digestible starch (SDS) of the starch component of corn flour, in the context of the present invention, is determined as already described above for corn starches after the corn starch has been isolated from the corn flour. Methods for isolation of corn starch from corn flour are known to those skilled in the art. Preferably, the corn starch is isolated from the corn flour using the method described herein below "extraction of corn starch".

In a further embodiment of the above described process according to the invention, the reduction of the percentage weight fraction of rapidly digestible starch (RDS) of the starch component in corn flour compared with to the corresponding corn starches of flours of wild type corn plants, are coupled with the increase of the percentage weight fraction of resistant starch (RS) of the starch component in corn flour compared with corresponding corn starches from flours or wild type corn plants and/or with the increase of the percentage weight fraction of slowly digestible starch (SDS) of the starch component in corn flour compared with the starch component of corresponding corn flours of amylose-extender (ae) corn plants.

A further object of the present invention is to provide methods by which the thermal stability of corn flour can be increased.

The present invention therefore relates to a process for producing corn flour in which the thermal stability of the corn flour is increased, which comprises expressing a heterologous starch synthase II in a corn plant that has an amylose content between 15% by weight and 40% by weight, preferably between 18% by weight and 35% by weight, and particularly preferably between 20% by weight and 30% by weight, and subsequently milling the corn plant or parts of this corn plant that express the heterologous starch synthase II to give corn flour.

The present invention further relates to a process for increasing the thermal stability of corn flour which comprises expressing a heterologous starch synthase II in a corn plant that has an amylose content between 15% by weight and 40% by weight, preferably between 18% by weight and 35% by weight, and particularly preferably between 20% by weight and 30% by weight, and subsequently milling the corn plant or parts of this corn plant that express the heterologous starch synthase II to give corn flour.

The expression "increasing the thermal stability", in the context of the present invention, is to be taken to mean increasing the DSC T-onset temperature of the corn starch/corn flour by at least 5° C., preferably by 5° C. to 12.5° C., particularly preferably by 7° C. to 10° C., and/or increasing the DSC T-peak temperature by at least 4° C., preferably by 4° C. to 11° C., particularly preferably by 6° C. to 9° C., in comparison with the corresponding corn plant that does not express a heterologous starch synthase II, preferably compared with the corresponding wild type corn plant.

In a further embodiment, the "increase of thermal stability" is taken to mean an increase of the DSC T-onset temperature of the corn starch/corn flour by at least 1.5° C., preferably by 2° C. to 7° C., particularly preferably by 3° C. to 5° C., and/or an increase of the DSC T-peak temperature by at least 2° C., preferably by 3° C. to 7° C., particularly preferably by 4° C. to 6° C., compared with corresponding corn plants that do not express a heterologous starch synthase II, preferably compared with corresponding wild type corn plants.

The "DSC T-onset" temperature and also the "DSC T-peak" temperature of the corn flour are determined in the context of the present invention likewise by the method described below ("thermal analysis of corn flour/corn starch by means of differential scanning calorimetry (DSC)").

In many thermal processing operations and applications, the use of granular corn starches or corn flours containing such granular corn starches is desirable. Therefore, increasing the DSC T-onset temperature or T-peak temperature of corn starches and corn flours by the process according to the invention is particularly advantageous. By this means the retention of the starch granule structure is ensured even at elevated process temperatures.

In a further embodiment, the present invention relates to a process for producing corn flour in which the thermal stability of the corn flour is increased and/or the percentage weight fraction of resistant starch (RS) in the corn flour is increased and/or the percentage weight fraction of rapidly digestible starch (RDS) in the corn flour is decreased, which comprises expressing a heterologous starch synthase II in a corn plant that has an amylose content between 15% by weight and 40% by weight, preferably between 18% by weight and 35% by weight, and particularly preferably between 20% by weight and 30% by weight, and subsequently milling the corn plant or parts of this corn plant expressing the heterologous starch synthase II to give corn flour.

In a further embodiment, the present invention relates to a process for increasing the thermal stability of corn flour and/or increasing the percentage weight fraction of resistant starch (RS) in corn flour and/or for decreasing the percentage weight fraction of rapidly digestible starch (RDS) in corn flour, which comprises expressing a heterologous starch synthase II in a corn plant that has an amylose content between 15% by weight and 40% by weight, preferably between 18% by weight and 35% by weight, and particularly preferably between 20% by weight and 30% by weight, and subsequently milling the corn plant or parts of this corn plant expressing the heterologous starch synthase II to give corn flour.

In a particularly preferred embodiment of the process of the invention, the heterologous starch synthase II is expressed in wild type corn plants that have an amylose content between 20% by weight and 30% by weight.

In a further, particularly preferred, embodiment of the process according to the invention, the increase of thermal stability of corn flour and/or the increase of the percentage weight fraction of resistant starch (RS) in corn flour and/or the reduction of the percentage weight fraction of rapidly digestible starch (RDS) in corn flour is related to the respective properties of the corn flour of corresponding corn flours of wild type corn plants.

Starch-storage parts of plants can be processed to give flours. For production of corn flours, the endosperm-containing corn kernels are milled and sieved. Starch is a main component of the endosperm. The corn starch of the invention is, in addition to proteins and lipids, the essential component of the corn flour modified according to the invention (approximately 65 to 75% by weight of the flour dry weight). The properties of the corn flours modified according to the invention are therefore greatly affected by the corn starch that is modified according to the invention and present in the corn flour.

The expression "corn flour", in the context of the present invention, is to be taken to mean a powder obtained by milling corn kernels. If appropriate, the corn kernels are dried before milling and, after milling, are comminuted and/or sieved.

The RS-amylomaize starches described in the prior art have the disadvantage of poor processing properties, because these starches scarcely gelatinize, have an increased tendency to retrogradation, a low swelling capacity and are poorly soluble in water. For applications in which only gelatinized starches are usable, or the tendency to retrogradation is to be decreased (for example for avoiding staling processes in bakery products), or a higher swelling capacity or a higher solubility are required, the amylomaize starches are therefore either entirely unsuitable, or they must in addition be chemically modified in order to set the desired properties.

Using the process of the invention it is now possible to provide corn starches and corn flours which have advantageous digestion properties (increased RS content, decreased content of RDS) and/or an increased thermal stability and/or, compared with amylomaize starches, a significantly increased gelatinization, a decreased tendency to retrogradation, an increased swelling capacity and/or an increased solubility.

A particular advantage of the processes according to the invention is decreasing the fraction of rapidly digestible flour or starch, since a rapid release of relatively large amounts of glucose and its absorption via the small intestine epithelium leads to an abrupt increase of the blood sugar level. As a consequence thereof, secretion of insulin occurs (insulin response). The continuous consumption of foods having a high glycemic charge and the resultant insulin secretion is suspected to be a risk factor in the development of diseases such as high blood pressure, overweight, heart disorders and diabetes type II.

Material and Methods

In the examples, the following methods were used. These methods can be used to carry out the process of the invention, they are specific embodiments of the present invention, but do not restrict the present invention to these methods.

1) Plant Material and Cultivation

Corn plants: *Zea mays*, variety A188

The corn plants were cultivated in the greenhouse under the following conditions:

Substrate:
  Special mixture for seeding
  80% light peat
  20% dark peat
  100 kg/m³ of sand
  40 kg/m³ of moist clay
  Structure: fine
  pH: 5.3-6.1
  Base fertilization: 2 kg/m³ 12-12-17 (+2) and 100 g/m³ of Radigen (Theraflor GmbH; Iserlohn; Germany)
Pots: 10 l containers
Planting density: Max. 6 plants/m²
Fertilization:
  1 TAB Plantosan 4 g (20-10-15+6) in the 4-leaf stage
  1 TAB Plantosan after a further 3 weeks
Temperature: Day 22-25° C./night 16° C.
Light: 18 hours, 350-400 µEinstein/s/m
Relative humidity: 50% rh.
Plant protection measures: as required insecticides: for example: Vertimec (Syngenta), Confidor® (BayerCropScience)

2) Origin of the Sequences and Constructs Used for the Transformation

For transformation of corn, use was made of the sequence Ta_SSIIa from wheat. It performed isolation and cloning as described in international patent application WO 97/45545 (under the then designation "pTaSS1"). The transformation vector pJH77 used is described in example 1.

3) Transformation and Regeneration of Corn Plants

Corn plants were transformed and regenerated by the method described by Ishida et al. (1996 Nature Biotechnology Vol. 14: 745-750)

4) Processing of Corn Kernels

For generation of sufficient amounts of analysis material, corn plants were grown under greenhouse conditions and after reaching complete ripeness, the cobs were harvested. For further drying, the ripe (that is to say fully developed) corn cobs were stored for 3-7 days at 37° C.

Subsequently, the kernels were taken off from the cobs. These served as starting material for analysis of the whole kernel, such as, for example, kernel weight.

5) Analysis of the Level of Expression of Starch Synthase II by RTPCR

The expression of starch synthase IIa from wheat in corn was studied by RTPCR. For this, for each independently transgenic event, four ripe corn kernels were studied. For homogenization, the corn kernels were shaken in the 1.5 ml Eppendorf vessel with a 4.5 mm steel ball in a Retsch mill (model MM300) for 30 seconds at a frequency of 30 Hertz. Subsequently the RNA was isolated by means of a "Plant RNAeasy" Quiagen Kit, according to the manufacturer's instructions (Plant RNAeasy, Quiagen, Germany). On the basis of a PCR with a previous reverse transcriptase step, the relative expression of the SS2 gene in den transgenic plants can be determined.

Primer Sequences:

1. Ta_SS2-F4:   5'-gAA gAA gCT CCA AAg CCA AA-3'
                (SEQ ID No. 3)

2. Ta_SS2-R4:   5'-ggC TCC TCg AAA CCA ATg TA-3'
                (SEQ ID No. 4)

3. Ta_SS2-FAM:  5'-TCT TgA AAT CCC AAA ggT CTT
                CTT gTA-3'
                (SEQ ID No. 5)

1a. 18S-F1:     5'-gTC ATC AgC TCg CgT TgA CT-3'
                (SEQ ID No. 6)

2a. 18S-R1:     5'-TCA ATC ggT Agg AgC gAC g-3'
                (SEQ ID No. 7)

3a. 18S-VIC:    5'-ACg TCC CTg CCC TTT gTA CAC
                ACC gC-3'
                (SEQ ID No. 8)

PCR reaction batch (QUIAGEN OneStep RT-PCR Kit):
Final Concentrations:
  RNA (50-500 ng)
  1× Quiagen buffer
  1× Q-solution
  0.4 mM dNTPs
  0.5 mM MgCl₂
  40 SYBR GREEN
  0.11 µM TagMan probe
  0.3 µM Forward Primer
  0.3 µM Reverse Primer
  1.2 µl Quiagen Enzyme mix
Conditions (PE Applied Biosystems ABI PRISM 7700):

| | | |
|---|---|---|
| 30 min | 60° C. | |
| 15 min | 95° C. | |
| 30 sec | 94° C. | |
| 30 sec | 60° C. | } 35 cycles |
| 60 sec | 72° C. | |

The PCR is quantified on the basis of calculation of the fluorescence threshold value, what is termed the threshold cycle or CT value. The CT value is that PCR cycle in which the reporter fluorescence significantly exceeds the background fluorescence. At the start of the PCR reaction, only the base fluorescence or background fluorescence is measured, since the reporter fluorescence is usually not detectable owing to the low template concentration in the reaction vessel during the first PCR cycles. Quantification of the amount of DNA is not based on absolute amounts of PCR product, but on the kinetics of the PCR reaction. The CT value is taken as guideline of this, since at this time point the amplification is exponential. In parallel thereto, in each PCR run, known amounts of template are amplified, so that it is possible to compare what amount of template is obtained at what CT value. A standard curve can be prepared therefrom on the basis of which the template concentration can be concluded.

For calculation of the levels of expression, the following formula applies:

$$\frac{X_{N,q}}{X_{N,cb}} = (1+E)^{-\Delta\Delta Ct} = 2^{-\Delta\Delta Ct} \text{(for } E=1\text{)}$$

$X_N$=normalized amount of target
E=efficiency of the PCR
$X_N$=normalized amount of target
$\Delta C_T$=difference between $C_T$ values of target gene and reference This gives: $X_N$=K $(1+E)^{-\Delta C_T}$ For each sample q which is compared with the calibrator cb, the following applies:

$$X_{N,q} = K(1+E)^{-\Delta C_{T,q}}$$

$$X_{N,cb} = K(1+E)^{-\Delta C_{T,cb}}$$

6) Determination of SSII Activity by Means of an Activity Gel

The various starch synthase activities in unripe corn kernels were detected by means of activity gels (zymograms), in which protein extracts are separated in a polyacrylamide gel under native conditions and are subsequently incubated with appropriate substrates. The reaction product formed (starch) was stained with Lugol's solution (2% (w/v) KI; 0.2% (w/v) $I_2$) in the gel.

Individual unripe corn kernels (approximately 15 days after blossom, measured from the day of start of blossom) were shock-frozen in liquid nitrogen and homogenized in 150-200 µl of cold extraction buffer (50 mM Tris/HCl pH 7.6, 2.5 mM EDTA, 2 mM DTT, 4 mM PMSF, 0.1% (w/v) glycogen, 10% (v/v) glycerol). After centrifugation (15 min, 13000 g, 4° C.), the clear supernatant was transferred to a fresh reaction vessel and one aliquot of the extract was used to determine the protein content according to Bradford (1976, Anal Biochem 72: 248-254).

The protein extracts were separated by means of a continuous 7.5% polyacrylamide gel (7.5% AA/BAA 37.5:1; 25 mM Tris/HCl pH 7.6, 192 mM glycine, 0.1% (w/v) APS, 0.05% (v/v) TEMED) using one times concentrated running buffer (25 mM Tris/HCl, 192 mM glycine). Before the gels are loaded there is a preliminary run to remove free radicals for 30 minutes at 8 mA and 4° C. For each sample, 30 µg of protein were applied and the electrophoresis was carried out for 2-2.5 hours at 4° C.

Thereafter, the gels were incubated overnight at room temperature with constant shaking in 15 ml of Incubation buffer (0.5M sodium citrate pH 7.0, mM potassium acetate, 2 mM EDTA, 2 mM DTT, 0.1% (w/v) amylopectin, 50 mM tricine/NaOH pH 8.5, 1 mM ADP-glucose). The starch formed was stained using Lugol's solution.

To determine how many times the activity of a protein having the activity of a starch synthase II is increased compared with corresponding wild type plants which have not been genetically modified, protein extracts of the genetically modified lines were in each case sequentially diluted and separated by electrophoresis in accordance with the above described method. The further steps were performed as described above. After the zymograms were stained with Lugol's solution, optical comparison was carried out of the intensity of the stained products produced by a protein having the activity of a starch synthase II (indicated in FIG. 2 by an arrow) for the various dilutions of the protein extracts of genetically modified plants with the relevant products of the undiluted wild type protein extract. Since the intensity of staining of the products is directly correlated with the activity of a protein having the activity of a starch synthase II, bands of the products having the same intensities have the same activity. If the band of the product of a protein having the activity of a starch synthase II in the diluted protein extract has the same intensity as the relevant band of the product from corresponding undiluted protein extract from wild type plants, the dilution factor corresponds to the degree of increase of activity in the relevant genetically modified plant.

7) Extraction of Corn Starch

Corn starch was extracted on the basis of the method described by the corn refiners association (http://www.corn.org/) for wet starch extraction. 10-50 g of corn kernels are weighed out and to disintegrate the protein matrix are incubated in an excess with 0.2% strength sulfurous acid for 3 days at 50° C. The kernels were then washed with water and briefly dried. Comminution was performed in a Retsch ultracentrifuge mill ZM100 using a 2 mm sieve. The comminuted material was transferred to a glass beaker, admixed with 20% strength NaCl solution and allowed to stand for at least 30 min. In this case the starch sediments and the lipid bodies float. The upper layer (germ) was poured off and the sediment resuspended in a residual supernatant. Subsequently, the starch was further purified by a plurality of sieving steps. First using a 500 µm test sieve (DIN 4188), subsequently using a 200 µm Retsch analysis sieve (DIN 4188) and finally the sample was passed through a 125 µm sieve (Iso 3310-1) and rinsed with NaCl (2-3 l) using a pressure spray system until the drops under the sieve no longer contained starch. This prepurified starch was sedimented overnight at room temperature and subsequently the supernatant down to approximately 5 mm above the sediments was poured off. The starch was transferred to a centrifuge beaker and centrifuged in a Heraeus Varifuge at room temperature with 3500 rpm for 10 min. Subsequently, the upper starch-protein layer (mostly different in color) was scrapped off and discarded.

A plurality of washing steps followed hereinafter, first using 0.2M sodium acetate pH 4.6 (centrifugation see above 5 min), wherein the upper starch-protein layer was again scrapped off. Subsequently thereto, a digest was made up in 0.2M sodium acetate pH 4.6 containing 1% Bromelain and 1% Pepsin in each case and was incubated at 37° C. for one hour on the rotator (vertical shaker). Subsequently the batch was centrifuged (see above) and the supernatant discarded. The upper starch-protein layer was again discarded and the pellet resuspended with mains water and centrifuged (see above 3000 rpm). A renewed mechanical separation followed of the protein layer which is situated on the pellet and generally clearly delimited. Four further wash steps with water followed, as described above. Subsequently, the pellet was washed four times with 80% technical ethanol and centrifuged (see above 3000 rpm). Finally, the batch was washed once with acetone in order to defat the starch and dried for two days at room temperature in a fume cupboard.

8) Preparation of Corn Flour/Corn Starch for Studying the Amylopectin Side Chain Distribution by Means of High Pressure Anion-Exchange Chromatography Per sample, 10 mg of corn flour or corn starch were weighed out into a 2 ml Eppendorf cup and admixed with 250 µl of 90% (v/v) DMSO. After the sample was dissolved with shaking at 60° C., 375 µl of water were added and the batch was incubated for one hour at 95° C. To 200 µl of the batch, 300 µl of 16.7 mM sodium acetate pH 3.5 and also 0.5 U of isoamylase from *Pseudomonas* sp. (Megazyme; Bray, Ireland) were added. After incubation for 24 hours at 37° C., a further 0.5 U of isoamylase was added and the incubation was continued for a further 24 hours.

For the chromatography, 100 µl of the batch was diluted 1:5 with water and subsequently filtered through Ultrafree-MC Filtertubes (Millipore). About 90 µl of the filtrate was injected.

Chromatography Method:
HPLC unit:
  GP 50 Dionex Gradient Pump
  ED 50 Dionex Electrochem. Detector/PAD
  AS 50 Autosampler
  column oven
Column: Dionex CarboPac PA 100 4×250 mm (P/N 046110) with Guard Column PA 100 4×50 mm (P/N 046115)
Equipment Configuration:

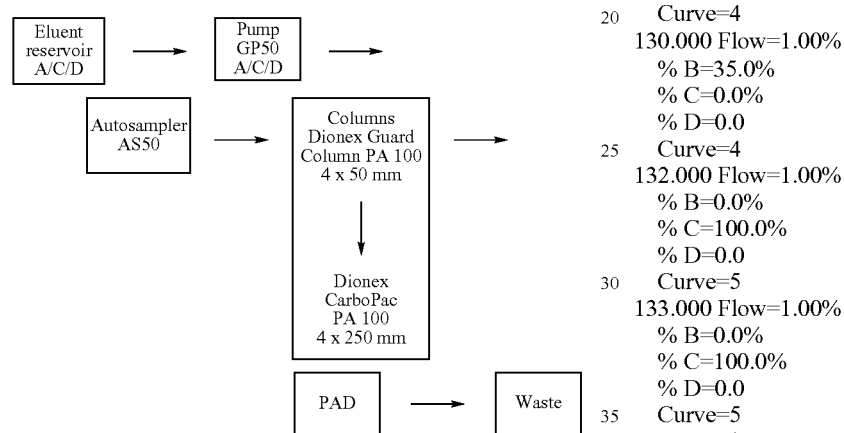

HPAEC Program:
  Pressure.LowerLimit=50
  Pressure.UpperLimit=3500%
  % A.Equate="NaOH 0.15 M"
  % B.Equate="NaOAc 1.0 M"
  % C.Equate="NaOAc 1.0 M in NaOH 0.15 M"
  % D.Equate="Millipore Water"
  ECD.Data_Collection_Rate=1.0
  Waveform Time=0.00, Potential=0.05
  Waveform Time=0.20, Potential=0.05, Integration=Begin
  Waveform Time=0.40, Potential=0.05, Integration=End
  Waveform Time=0.41, Potential=0.75
  Waveform Time=0.60, Potential=0.75
  Waveform Time=0.61, Potential=−0.15
  Waveform Time=1.00, Potential=−0.15
  Cell=On
  Flush Volume=500
  Wait FlushState
  NeedleHeight=2
  CutSegmentVolume=10
  SyringeSpeed=4;
  Cycle=0
  Wait For Temperature=False
  Wait SampleReady
0.000 Flow=1.00%
  % B=0.0%
  % C=0.0%
  % D=0.0
  Curve=5
  Load
  Inject
  Wait
  ECD.Autozero
  ECD_1.AcqOn
  Flow=1.00%
  % B=0.0%
  % C=0.0%
  % D=0.0
  Curve=5
5.000 Flow=1.00%
  % B=11.0%
  % C=0.0%
  % D=0.0
  Curve=5
  Flow=1.00%
  % B=11.0%
  % C=0.0%
  % D=0.0
  Curve=4
130.000 Flow=1.00%
  % B=35.0%
  % C=0.0%
  % D=0.0
  Curve=4
132.000 Flow=1.00%
  % B=0.0%
  % C=100.0%
  % D=0.0
  Curve=5
133.000 Flow=1.00%
  % B=0.0%
  % C=100.0%
  % D=0.0
  Curve=5
142.000 Flow=1.00%
  % B=0.0%
  % C=0.0%
  % D=0.0
  Curve=5
143.000 Flow=1.00%
  % B=0.0%
  % C=0.0%
  % D=95.0
  Curve=5
152.000 Flow=1.00%
  % B=0.0%
  % C=0.0%
  % D=95.0
  Curve=5
  ECD_1.AcqOff
  End The data were evaluated using a Dionex Chromeleon v6.60 (Dionex Corporation, Sunnyvale, Calif., USA). The handbook "Tutorial and User Manual" of Version 6.60, March 2004, can be obtained via Dionex, or can be downloaded via the Homepage (http://www.dionex.com).

For comparison of the chromatograms with one another, for each chromatogram the identified peaks of the different maltooligasaccharides were mean-value normalized (sum of all peak areas=1). Evaluation was performed on the basis of "force common baseline", as described in Dionex Chromeleon v.6.60 for "log baseline". In this case the log baseline is set just before the first side chain peak and up to the last evaluable peak of the shortest chromatogram of a measurement passage, from this the last evaluable peak for all chromatograms was calculated.

9) Thermal Analysis of Corn Flour/Corn Starch by Means of Differential Scanning Calorimetry (DSC)

Weighed samples of about 10 mg (dry weight) of corn flour or corn starch were placed in stainless steel pans (Perkin Elmer, "Large Volume Stainless Steel Pans" [03190218], Volume 60 µl) with an excess, preferably a 2-fold excess of bidistilled water (preferably 20 µl) and hermetically sealed using a press. The sample was heated from 20° C. to 150° C. in a Diamond DSC apparatus (Perkin Elmer) at a heating rate of 10° C./min. In this method an empty closed stainless steel pan was used as reference. The system was calibrated with known amounts of indium.

The data analysis was carried out using the Pyris software program (Perkin Elmer, Version 7.0). Evaluable raw data were further processed by analysis of the individual peaks of the first order phase transitions to T-onset (° C.), T-peak (° C.), T-end (° C.) and dH (J/g) (the standard in this case is the straight baseline).

DSC T-onset is characterized in this case as the intersection between the extrapolation of the baseline and the tangent to the ascending flank of the peak through the inflection point. It characterizes the start of the phase transition.

The maximum temperature DSC T-peak is termed the maximum temperature at which the DSC curve reaches a maximum (that is to say the temperature at which the first derivative of the curve is zero).

In the case of the function used in Pyris (calculated peak area) a start temperature and a final temperature is entered by hand for the baseline fit.

10) Determination of the Apparent Amylose Content

The apparent amylose content is determined on the basis of the method of Juliano (1971, Cereal Science Today 16 (10): 334-340).

For each sample, 50 mg of corn flour were weighed out twice into 100 ml Erlenmeyer flasks and moistened sequentially with 1 ml of 95% ethanol and 9 ml of 1M NaOH.

In parallel, to establish a standard curve, flasks containing defined amounts of (pure) amylose were treated in the same manner as the flour samples. For this purpose, a native corn starch from Sigma-Aldrich (order no. S4126, batch number: #015K0144) can also be used, for example, which, according to the manufacturer's specification, has an amylose content of 27% by weight and an amylopectin content of 73% by weight. The flasks, for thorough mixing, were briefly swirled and subsequently incubated for 20 minutes in a boiling water bath with gentle shaking. After cooling for 5-10 minutes at RT, the volume was made up to 100 ml with water.

One aliquot at 100 µl was admixed with 1 ml of measurement solution (10 mM acetic acid, 0.004% (w/v) $I_2$; 0.04% (w/v) KI), mixed well and the absorption was determined at 620 nm against a corresponding blank. The amylose content was calculated using the amylose standards which are used to establish a calibration curve.

11) Analysis of Corn Starch by Means of a Rapid Visco Analyser (RVA)

It is based on the fact that a suspension of water and corn starch is subjected to a defined temperature and shearing protocol and during this the viscosity of the suspension is continuously recorded. The measuring instrument used is an RVA Super3 from Newport Scientific (Macclesfield, UK) with the corresponding software "Thermocline for Windows", Version 2.3.

For the analysis, 2.5 g of corn starch (weighed as pure dry weight of the sample material, corrected to 0% moisture) were weighed out into a measurement vessel, admixed with 25 ml of water and the measuring instrument was plugged into the apparatus after insertion of a stirrer.

The following temperature and shearing profile was applied:

| Time | Type | Value |
| --- | --- | --- |
| 00:00:00 | Temp | 50° C. |
| 00:00:00 | Speed | 960 rpm |
| 00:00:10 | Speed | 160 rpm |
| 00:01:00 | Temp | 50° C. |
| 00:04:45 | Temp | 95° C. |
| 00:07:15 | Temp | 95° C. |
| 00:11:00 | Temp | 50° C. |
| 00:17:00 | End of test | |

After termination of the measurement, the following parameters were determined:

Peak viscosity (highest viscosity between 2 and 7 minutes of measuring time)

Trough viscosity (lowest viscosity between 7 and 12 minutes of measuring time)

Final viscosity (viscosity at the end of the measurement)

Breakdown=peak−trough

Setback=final−trough

Pasting temperature (temperature at which the viscosity changes by more than 50 cP in a time interval of 0.5 minutes)

Peak time (time at which the peak viscosity is achieved)

12) Determination of the Content of Phosphate in the C6 Position (C6-P Content)

In the starch, positions C3 and C6 of the glucose units can be phosphorylated. For determination of the C6-P content of the starch (modified according to Nielsen et al., 1994, Plant Physiol. 105: 111-117) 50 mg of corn flour/starch were hydrolyzed in 500 µl of 0.7M HCl for 4 h at 95° C. with constant shaking. Subsequently, the batches were centrifuged for 10 min at 15 500 g and the supernatants were freed from suspended matter and haze by means of a filter membrane (0.45 µM). 20 µl of the clear hydrolysate were mixed with 180 µl of imidazole buffer (300 mM imidazole, pH 7.4; 7.5 mM $MgCl_2$, 1 mM EDTA and 0.4 mM NADP). The measurement was carried out in the photometer at 340 nm. After determination of the base absorption, the enzyme reaction was started by adding 2 units of glucose-6-phosphate dehydrogenase (from *Leuconostoc mesenteroides*, Boehringer Mannheim). The change in absorption is based on an equimolar reaction of glucose-6-phosphate and NADP to give 6-phosphogluconate and NADPH, wherein the formation of NADPH is determined at the abovementioned wavelength. The reaction was followed until a plateau was reached. The result of this measurement gives the content of glucose-6-phosphate in the hydrolysate. From the identical hydrolysate, on the basis of the content of glucose released, the degree of hydrolysis was determined. This is used in order to relate the content of glucose-6-phosphate to the fraction of hydrolyzed starch from the fresh weight. For this, 10 µl of hydrolysate were neutralized with 10 µl of 0.7M NaOH and subsequently diluted 1:100 with water. 4 µl of this dilution were admixed with 196 µl of measurement buffer (100 mM imidazole pH 6.9; 5 mM $MgCl_2$, 1 mM ATP, 0.4 mM NADP) and used for determination of the base absorption. The reaction was started by addition of 2 µl of enzyme mix (hexokinase 1:10; glucose-6-phosphate dehydrogenase from yeast 1:10 in measurement buffer) and followed at 340 nm to the plateau. The principle of measurement corresponds to that of the first reaction.

The result of this measurement gives the amount of glucose (in mg) which was released from the starch present in the starting material in the course of the hydrolysis.

Subsequently, the results of both measurements were related to express the content of glucose-6-phosphate per mg of hydrolyzed starch. Contrary to a relation of the amount of glucose-6-phosphate to the fresh weight of the sample, this calculation only relates to the amount of glucose-6-phosphate to the part of the starch which completely hydrolyzed glucose, and therefore is also to be considered as source for glucose-6-phosphate.

13) Determination of the Resistant Starch Fraction (Digestibility)

The resistant starch fraction is determined according to the method described in Englyst et al. (Europ. J. of Clinical Nutrition 46 (Suppl. 2), (1992), S33-50)) (see, in particular, the following sections from Englyst et al., pages S35-S36: "Reagents, Apparatus, Spectrophotometer"; pages S36-S37, paragraph "Measurement of free glucose (FG)"; page S38, paragraph "Measurement of RDS and SDS").

The method of Englyst et al. can alternatively be carried out as described by Zhang et al. (Biomacromolecules 7, (2006), 3252-3258, in particular page 3253: Methods. Enzymatic Starch Hydrolysis).

On laboratory scale, the method of Englyst et al. can be carried out in the following manner using corn starch or corn flour:

For production of the enzyme solution, 1.2 g of pancreatin (Merck) are extracted in 8 ml of water for 10 minutes at 37° C. After centrifugation (10', 3000 rpm; RT), 5.4 ml of the supernatant are mixed with 84 U of amyloglucosidase (Sigma-Aldrich, Taufkirchen) and made up with water to a final volume of 7 ml.

In parallel, 10 mg (dry weight) of corn flour or corn starch per sample in a 2 ml reaction vessel are admixed with 0.75 ml of sodium acetate buffer (0.1M sodium acetate pH 5.2; 4 mM $CaCl_2$) and incubated at 37° C. for 5 minutes to warm the batch.

The starch digestion is started by adding in each case 0.25 ml of enzyme solution per batch. The control used is a batch to which water is added instead of enzyme solution. After 20, 60 and 120 minutes, aliquots of 100 µl are taken and placed directly into four times the volume of ethanol, as a result of which the enzymes are inactivated. This dilution is used to measure the glucose content.

For this, 2 µl of diluted sample are mixed with 200 µl of measurement buffer (100 mM imidazole/HCl pH 6.9, 5 mM $MgCl_2$, 1 mM ATP, 2 mM NADP) and the absorption of the sample is determined at 340 nm. The reaction of the glucose is started by addition of 2 µl of enzyme mix (10 µl of hexokinase, 10 µl of glucose-6-phosphate dehydrogenase, 80 µl of measurement buffer) and the equimolar conversion of NADP to NADPH at 340 nm is followed until a plateau is reached. The amounts of glucose determined are related to the amount weighed out and give the fraction of the sample which was released as glucose after the corresponding period.

The examples hereinafter illustrate the invention.

EXAMPLES

Example 1

Production of the Vector pJH77 for Expression of a Starch Synthase II from Wheat in Corn The vector pJH77 (see FIG. 1) has the genetic elements described in table 1:

TABLE 1

Description of the genetic elements of JH77

| Nt positions | Orientation | Origin |
|---|---|---|
| 6600-6623 | | RB: right-hand border of T-DNA from *Agrobacterium tumefaciens* (Zambryski, 1988) |
| 6624-6909 | | remaining TL-DNA of pTiAch5, which flanks the right-hand border (Gielen et al., 1984) |
| 6910-7285 | Anticlockwise | 3' nos: sequence comprising the 3' untranslated region of the nopalin synthase gene of T-DNA of the plasmid pTiT37 (Depicker et al., 1982) |
| 7286-9685 | Anticlockwise | ss2aTa: coding sequence of the starch synthase isoform 2a gene (ss2a) from *Triticum aestivum* (wheat) (SEQ ID No. 1) |
| 9686-10437 | Anticlockwise | intron1 ubi1 Zm: first intron of the ubiquitin-1 gene (ubi1) from *Zea mays* (Christensen et al., 1992). |
| 10438-11478 | Anticlockwise | PglobulinOs: sequence comprising the promoter region of the globulin gene from *Oryza sativa* (rice) (Hwang et al. (2002)) |
| 11479-13261 | Clockwise | Pact1Os: sequence comprising the promoter region of the actin 1 gene from *Oryza sativa* (rice) (Mc Elroy et al., 1990). |
| 13262-13739 | Clockwise | intron1 act1 Os: first intron of the actin 1 gene from *Oryza sativa* (rice) (Mc Elroy et al., 1990). |
| 13740-14291 | Clockwise | bar: coding sequence of the phosphinothricin acetyltransferase gene from *Streptomyces hygroscopicus* (Thompson et al. (1987)) |
| 14292-14561 | Clockwise | 3' nos: sequence comprising the 3' untranslated region of the nopalin synthase gene of T-DNA of the plasmid pTiT37 (Depicker et al., 1982) |
| 14562-296 | | remaining TL-DNA of pTiAch5, which flanks the left-hand border (Gielen et al., 1984) (Gielen et al., 1984) |
| 297-320 | | LB: left-hand border of T-DNA from *Agrobacterium tumefaciens* (Zambryski, 1988) |

REFERENCES

Christensen A. H., Sharrock R. A., Quail P. H. (1992). Maize polyubiquitin genes: structure, thermal pertubation of expression and transcript splicing, and promoter activity following transfer to protoplasts by electroporation. Plant Molecular Biology, 18, 675-689.

Depicker A., Stachel S., Dhaese P., Zambryski P., Goodman H. M. (1982). Nopaline synthase: transcript mapping and DNA sequence. Journal of Molecular and Applied Genetics, 1, 561-573.

Gielen J.; De Beuckeleer M.; Seurinck J.; Deboeck F.; De Greve H.; Lemmers M.; Van Montagu M.; Schell J. (1984). Isolation of an efficient actin promoter for use in rice transformation. The EMBO journal, 3, 835-846

Hwang Y.-S., Yang D., McCullar C., Wu L., Chen L., Pham P., Nandi S., Huang N. (2002). Analysis of the rice-endosperm-specific globulin promoter in transformed rice cells. Plant Cell Rep 20, 842-847.

Leroux B., Pelissier B., Lebrun M. (1996). Chimeric herbicide resistance gene. U.S. Pat. No. 5,559,024 (24 Sep. 1996), RHONE POULENC AGROCHIMIE (FR).

Mc Elroy D., Zhang W., Cao J., Wu R. (1990). Isolation of an efficient actin promoter for use in rice transformation. The Plant Cell, 2, 163-171.

Thompson C. J., Rao Movva N., Tizard R., Crameri R., Davies J., Lauwereys M., Botterman J. (1987). Characterization of the herbicide resistance gene bar from *Streptomyces hygroscopicus*. The EMBO Journal, 6, 2519-2523.

Zambryski P. (1988). Basic processes underlying *Agrobacterium*-mediated DNA transfer to plant cells. Annual Review of Genetics, 22, 1-30.

Example 2

Production and Identification of Genetically Modified Corn Plants which have an Increased SSII Activity For production of genetically modified plants having an increased starch synthase II (SSII) activity, the T-DNA of plasmid pJH77 as described in Ishida et al. (1996, Nature Biotechnology 14 (6): 745-750) was transferred to corn plants using agrobacteria. The increase in SS2 activity was demonstrated in zymograms.

FIG. 2 shows zymograms of two genetically modified corn lines on the basis of which the SS2 activity was determined in comparison with the wild type. For this, total protein was extracted from unripe kernels (harvested 15 days after pollination), both from the wild type and also from the transgenic lines. The protein extracts of the transgenic lines were applied in a dilution series and thus the level of activity was compared with the intensity of the SS2 band of the wild type. The SS2 activity is here increased 5×.

Example 3

Analysis of the Starches and Flours of Genetically Modified Corn Plants which have an Increased SSII Activity Flours were produced from individual kernels. The individual kernels were analyzed by PCR. Kernels in which the SSII from wheat is present (hereinafter termed "transgenic") and kernels which do not express SSII from wheat (hereinafter termed "wild type") were identified, separated from one another and then in each case combined to form groups and flours were produced. The analysis was subsequently performed on these flours. For the production of starches, in each case 10 kernels of the wild type plants and 10 kernels of the transgenic corn plants were combined and starch was isolated in each case therefrom.

The starches/flours of the transgenic heterozygotic corn lines, compared with the starches/flours of the wild type corn plants, had an unchanged amylose content, an increased DSC T-onset temperature, an increased DSC T-peak temperature, an increased RS content and also a decreased RDS content.

Properties of the corn flours relative to the wild type (100%):

| Line | Amylose content in % wt | RS content in % wt | RDS content in % wt | DSC $T_{onset}$ in °C. | DSC $T_{peak}$ in °C. |
|---|---|---|---|---|---|
| Wild type (WT) A188 | 100 | 100 | 100 | 65-67° C. | 73°-75° C. |
| Transgenic line 1 | 100 | 120 | 90 | +5 | +4 |
| Transgenic line 2 | 100 | 130 | 83 | +7 | +6 |
| Transgenic line 3 | 100 | 150 | 70 | +10 | +9 |
| Transgenic line 4 | 100 | 200 | 50 | +12.5 | +11 |

Properties of the extracted, granular corn starches, in each case relative to the corresponding granular wild type starches:

a. Amylose content of the starch relative to the wild type (100%):

| Sample | Amylose content in % of wild type |
|---|---|
| Wild type plant (A188) | 100% |
| JH77-00701-2 | 105% |
| JH77-02101 | 97% | b. DSC data of the extracted starch (DSC analysis with 2-fold water excess) relative to the wild type

| Sample | T onset in °C. in comparison with wild type | T peak in °C. in comparison with wild type |
|---|---|---|
| Wild type plant (A188) | — | — |
| JH77-00701-2 | +4.3 | +4.98 |
| JH77-02101 | +4.2 | +4.81 |
| Hylon ®7 | +1.6 | +4.46 | c. RS, SDS and RDS content of the extracted starch relative to the wild type (100%):

| Sample | RS (in % of wild type) | SDS (in % of wild type) | RDS (in % of wild type) |
|---|---|---|---|
| Wild type plant (A188) | 100 | 100 | 100 |
| JH77-00701-2 | 440 | 70 | 37 |
| JH77-02101 | 405 | 74 | 41 |
| Hylon ® 7 | 714 | 26 | 33 |

The invention claimed is:

1. A process for increasing the percentage weight fraction of resistant starch (RS) in corn starch comprising the steps of:
   a) expressing a heterologous starch synthase II from the genus *Triticum* in a corn plant that synthesizes a starch having an amylose content between 15% by weight and 40% by weight, wherein the amino acid sequence of the heterologous starch synthase II has an identity of at least 86% with amino acids 322 to 351 of the amino acid sequence of SEQ ID No. 2 and an identity of at least 83% with amino acids 423 to 462 of the amino acid sequence of SEQ ID No. 2 and an identity of at least 70% with amino acids 641 to 705 of the amino acid sequence of SEQ ID No. 2, and
   b) subsequently extracting the starch, wherein the percentage weight fraction of resistant starch (RS) is increased by at least 10% compared with corn starches from corresponding corn plants which do not express a heterologous starch synthase II.

2. The process of claim 1, wherein the heterologous starch synthase II is expressed in a corn plant that synthesizes a starch having an amylose content between 18% by weight and 35% by weight.

3. The process of claim 1, wherein the heterologous starch synthase II is expressed in a corn plant that synthesizes a starch having an amylose content between 20% by weight and 30% by weight.

4. The process of claim 1, wherein the percentage weight fraction of resistant starch (RS) is increased by 100% to 500% compared with corn starches from corresponding corn plants that do not express a heterologous starch synthase II.

5. A process for producing corn flour in which the percentage weight fraction of resistant starch (RS) of the starch component in corn flour is increased comprising the steps of:
   a) expressing a heterologous starch synthase II from the genus *Triticum* in a corn plant that synthesizes a starch having an amylose content between 15% by weight and 40% by weight, wherein the amino acid sequence of the heterologous starch synthase II has an identity of at least 86% with amino acids 322 to 351 of the amino acid sequence of SEQ ID No. 2 and an identity of at least 83% with amino acids 423 to 462 of the amino acid sequence of SEQ ID No. 2, and an identity of at least 70% with amino acids 641 to 705 of the amino acid sequence of SEQ ID No. 2, and
   b) subsequently milling the corn plant that expresses heterologous starch synthase II, or parts of this corn plant, to produce corn flour.

6. The process of claim 5, wherein the heterologous starch synthase II is expressed in a corn plant that synthesizes a starch having an amylose content between 18% by weight and 35% by weight.

7. The process of claim 5, wherein the heterologous starch synthase II is expressed in a corn plant that synthesizes a starch having an amylose content between 20% by weight and 30% by weight.

8. The process of claim 5, wherein the percentage weight fraction of resistant starch (RS) of the starch component in corn flour is increased by 100%-500% compared with corn flour from corresponding corn plants that do not express a heterologous starch synthase II.

9. A process for increasing the thermal stability of corn starch comprising the step of: expressing a heterologous starch synthase II from the genus *Triticum* in a corn plant that synthesizes a starch having an amylose content between 15% by weight and 40% by weight, wherein the amino acid sequence of the heterologous starch synthase II has an identity of at least 86% with amino acids 322 to 351 of the amino acid sequence of SEQ ID No. 2 and an identity of at least 83% with amino acids 423 to 462 of the amino acid sequence of SEQ ID No. 2, and an identity of at least 70% with amino acids 641 to 705 of the amino acid sequence of SEQ ID No. 2, and wherein the resistant corn starch has increased thermal stability in comparison with corn starch produced from corn plants that do not express a heterologous starch synthase II.

10. The process of claim 9, wherein the heterologous starch synthase II is expressed in a corn plant that synthesizes a starch having an amylose content between 18% by weight and 35% by weight.

11. The process of claim 9, wherein the heterologous starch synthase II is expressed in a corn plant that synthesizes a starch having an amylose content between 20% by weight and 30% by weight.

12. The process of claim 9, wherein the increased thermal stability consists in an increase of the DSC T-onset temperature by 2° C. to 7° C. compared with corn starch from a corresponding corn plant that does not express a heterologous starch synthase II.

13. A process for producing corn flour in which the thermal stability of the corn flour is increased, comprising the steps of: expressing a heterologous starch synthase II from the genus *Triticum* in a corn plant that synthesizes a starch having an amylose content between 15% by weight and 40% by weight, and subsequently milling the corn plant that expresses heterologous starch synthase II, or parts of this corn plant, to give corn flour, wherein the amino acid sequence of the heterologous starch synthase II has an identity of at least 86% with amino acids 322 to 351 of the amino acid sequence of SEQ ID No. 2 and an identity of at least 83% with amino acids 423 to 462 of the amino acid sequence of SEQ ID No. 2, and an identity of at least 70% with amino acids 641 to 705 of the amino acid sequence of SEQ ID No. 2, wherein the corn flour produced by said process has increased thermal stability in comparison with corn flour produced from corn plants that do not express a heterologous starch synthase II.

14. The process of claim 13, wherein the heterologous starch synthase II is expressed in a corn plant that synthesizes a starch having an amylose content between 18% by weight and 35% by weight.

15. The process of claim 13, wherein the heterologous starch synthase II is expressed in a corn plant that synthesizes a starch having an amylose content between 20% by weight and 30% by weight.

16. The process of claim 13, wherein the increased thermal stability consists in an increase of the DSC T-onset temperature by 2° C. to 7° C. compared with the corresponding corn plant that does not express a heterologous starch synthase II.

17. A process for increasing the percentage weight fraction of resistant starch (RS) in corn starch comprising the steps of:

a) expressing a heterologous starch synthase II from the genus *Triticum* in a corn plant that synthesizes a starch having an amylose content of less than 40% by weight, wherein the amino acid sequence of the heterologous starch synthase II has an identity of at least 86% with amino acids 322 to 351 of the amino acid sequence of SEQ ID No. 2 and an identity of at least 83% with amino acids 423 to 462 of the amino acid sequence of SEQ ID No. 2 and an identity of at least 70% with amino acids 641 to 705 of the amino acid sequence of SEQ ID No. 2, and b) subsequently extracting the starch, wherein the percentage weight fraction of resistant starch (RS) is increased by at least 10% compared with corn starches from corresponding corn plants which do not express a heterologous starch synthase II.

18. The method of claim 1, wherein the percentage weight fraction of rapidly digestible starch (RDS) is reduced by at least 10% compared with corn starches from corresponding corn plants which do not express a heterologous starch synthase II.

19. The method of claim 1, wherein the percentage weight fraction of slowly digestible starch (SDS) is increased by at least 200% compared with corn starches from corresponding corn amylose-extender plants.

20. A method for retarding glucose release of a food comprising supplying food comprising a corn starch comprising a percentage weight fraction of slowly digestible starch (SDS) that is increased by at least 200% compared with corn starches from corresponding corn amylose-extender plants, wherein said corn starch is obtained from a corn plant expressing a heterologous starch synthase II from the genus *Triticum*, wherein said method retards glucose release of said food, and further wherein said food is a food in which continuous release of glucose is sought.

21. A method for reducing the feeling of hunger comprising supplying food comprising a corn starch comprising a percentage weight fraction of slowly digestible starch (SDS) that is increased by at least 200% compared with corn starches from corresponding corn amylose-extender plants, wherein said corn starch is obtained from a corn plant expressing a heterologous starch synthase II from the genus *Triticum*, wherein said method reduces the feeling of hunger, and further wherein said food is a food in which continuous release of glucose is sought.

22. The method of claim 20, wherein said food is food for endurance sports.

23. The method of claim 20, wherein said food is dietetic food.

24. The method of claim 21, wherein said food is food for endurance sports.

25. The method of claim 21, wherein said food is dietetic food.

26. A method of preparing a food comprising the step of adding a corn starch to a food in which continuous release of glucose is sought, wherein said corn starch has an amylose content between 18% by weight and 35% by weight, wherein said corn starch is obtained from a corn plant expressing a heterologous starch synthase II from the genus *Triticum*, wherein said heterologous starch synthase II has an amino acid sequence with an identity of at least 86% with amino acids 322 to 351 of the amino acid sequence of SEQ ID No. 2 and an identity of at least 83% with amino acids 423 to 462 of the amino acid sequence of SEQ ID No. 2 and an identity of at least 70% with amino acids 641 to 705 of the amino acid sequence of SEQ ID No. 2, wherein said corn starch comprises a percentage weight fraction of resistant starch (RS) that is increased by 100% to 500% compared with corn starches from corresponding corn plants that do not express a heterologous starch synthase II, and wherein said corn starch comprises a percentage weight fraction of slowly digestible starch (SDS) that is increased by 200% to 400% compared with corn starches from corresponding corn amylose-extender plants.

27. The method of claim 26, wherein said corn starch has a percentage weight fraction of rapidly digestible starch (RDS) is reduced by 10% to 75% compared with corn starches from corresponding corn plants which do not express a heterologous starch synthase II.

28. The method of claim 26, wherein said food is food for endurance sports.

29. The method of claim 26, wherein said food is dietetic food.

30. The method of claim 26, wherein said heterologous starch synthase II has an amino acid sequence comprising SEQ ID NO: 2.

* * * * *

SEQUENCE LISTING

<160> NUMBER OF SEQ ID NOS: 8

<210> SEQ ID NO 1
<211> LENGTH: 2400
<212> TYPE: DNA
<213> ORGANISM: Triticum aestivum

<400> SEQUENCE: 1

| | | | | | |
|---|---|---|---|---|---|
| atgtcgtcgg | cggtcgcgtc | cgccgcatcc | ttcctcgcgc | tcgcgtcagc | ctcccccggg | 60 |
| agatcacgca | ggcgggcgag | ggtgagcgcg | cagccacccc | acgccggggc | cggcaggttg | 120 |
| cactggccgc | cgtggccgcc | gcagcgcacg | gctcgcgacg | gagctgtggc | ggcgctcgcc | 180 |
| gccgggaaga | aggacgcggg | gatcgacgac | gccgccgcgt | ccgtgaggca | gccccgcgca | 240 |
| ctccgcggtg | gcgccgccac | caaggtcgcg | gagcgaaggg | atcccgtcaa | gacgctcgac | 300 |
| cgcgacgccg | cggaaggcgg | cgggccgtcc | ccgccggcag | cgaggcagga | cgccgcccgt | 360 |
| ccgccgagta | tgaacggcat | gccggtgaac | ggcgagaaca | aatctaccgg | cggcggcggc | 420 |
| gcgactaaag | acagcgggct | gcccacgccc | gcacgcgcgc | ccatccgtc | gacccagaac | 480 |
| agagcaccgg | tgaacggtga | aaacaaagct | aacgtcgcct | cgccgccgac | gagcatagcc | 540 |
| gaggccgcgg | cttcggattc | cgcagctacc | atttccatca | gcgacaaggc | gccggagtcc | 600 |
| gttgtcccag | ctgagaagac | gccgccgtcg | tccggctcaa | atttcgagtc | ctcggcctct | 660 |
| gctcccgggt | ctgacactgt | cagcgacgtg | gaacaagaac | tgaagaaggg | tgcggtcgtt | 720 |
| gtcgaagaag | ctccaaagcc | aaaggctctt | tcgccgcctg | cagcccccgc | tgtacaagaa | 780 |
| gaccttgggg | atttcaagaa | atacattggt | tcgaggagc | ccgtggaggc | caaggatgat | 840 |
| ggccgggctg | tcgcagatga | tgcgggctcc | tttgaacacc | accagaatca | cgactccgga | 900 |
| cctttggcag | gggagaatgt | catgaacgtg | gtcgtcgtgg | ctgctgagtg | ttctccctgg | 960 |
| tgcaaaacag | gtggtctggg | agatgttgcg | ggtgctctgc | ccaaggcttt | ggcaaagaga | 1020 |
| ggacatcgtg | ttatggttgt | ggtaccaagg | tatggggact | atgaagaagc | ctacgatgtc | 1080 |
| ggagtccgaa | atactacaa | ggctgctgga | caggatatgg | aagtgaatta | tttccatgct | 1140 |
| tatatcgatg | gagttgattt | tgtgttcatt | gacgctcctc | tcttccgaca | ccgtcaggaa | 1200 |
| gacatttatg | gggcagcag | acaggaaatt | atgaagcgca | tgattttgtt | ctgcaaggcc | 1260 |
| gctgttgagg | ttccatggca | cgttccatgc | ggcggtgtcc | cttatgggga | tggaaatctg | 1320 |
| gtgtttattg | caaatgattg | gcacacggca | ctcctgcctg | tctatctgaa | agcatattac | 1380 |
| agggaccatg | gtttgatgca | gtacactcgg | tccattatgg | tgatacataa | catcgctcac | 1440 |
| cagggccgtg | gccctgtaga | tgaattcccg | ttcaccgagt | tgcctgagca | ctacctggaa | 1500 |
| cacttcagac | tgtacgaccc | cgtgggtggt | gaacacgcca | actacttcgc | cgccggcctg | 1560 |
| aagatggcgg | accaggttgt | cgtggtgagc | cccgggtacc | tgtgggagct | gaagacggtg | 1620 |
| gagggcggct | gggggcttca | cgacatcata | cggcagaacg | actggaagac | ccgcggcatc | 1680 |
| gtcaacggca | tcgacaacat | ggagtggaac | cccgaggtgg | acgcccacct | caagtcggac | 1740 |
| ggctacacca | acttctccct | gaggacgctg | gactccggca | gcggcagtg | caaggaggcc | 1800 |
| ctgcagcgcg | agctgggcct | gcaggtccgc | gccgacgtgc | cgctgctcgg | cttcatcggc | 1860 |
| cgcctggacg | ggcagaaggg | cgtggagatc | atcgcggacg | ccatgccctg | gatcgtgagc | 1920 |
| caggacgtgc | agctggtgat | gctgggcacc | gggcgccacg | acctggagag | catgctgcag | 1980 |
| cacttcgagc | gggagcacca | cgacaaggtg | cgcgggtggg | tggggttctc | cgtgcgcctg | 2040 |
| gcgcaccgga | tcacggcggg | ggcggacgcg | ctcctcatgc | cctcccggtt | cgagccgtgc | 2100 |

-continued

```
gggctgaacc agctctacgc catggcctac ggcaccgtcc ccgtcgtgca cgccgtcggc    2160
ggcctcaggg acaccgtgcc gccgttcgac cccttcaacc actccgggct cgggtggacg    2220
ttcgaccgcg ccgaggcgca aagctgatc gaggcgctcg ggcactgcct ccgcacctac     2280
cgagacttca aggagagctg gagggccctc caggagcgcg gcatgtcgca ggacttcagc    2340
tgggagcacg ccgccaagct ctacgaggac gtcctcgtca aggccaagta ccagtggtga    2400
```

<210> SEQ ID NO 2
<211> LENGTH: 799
<212> TYPE: PRT
<213> ORGANISM: Triticum aestivum

<400> SEQUENCE: 2

```
Met Ser Ser Ala Val Ala Ser Ala Ala Ser Phe Leu Ala Leu Ala Ser
1               5                   10                  15

Ala Ser Pro Gly Arg Ser Arg Arg Ala Arg Val Ser Ala Gln Pro
            20                  25                  30

Pro His Ala Gly Ala Gly Arg Leu His Trp Pro Pro Trp Pro Pro Gln
            35                  40                  45

Arg Thr Ala Arg Asp Gly Ala Val Ala Ala Leu Ala Ala Gly Lys Lys
50                  55                  60

Asp Ala Gly Ile Asp Ala Ala Ala Ser Val Arg Gln Pro Arg Ala
65                  70                  75                  80

Leu Arg Gly Gly Ala Ala Thr Lys Val Ala Glu Arg Arg Asp Pro Val
            85                  90                  95

Lys Thr Leu Asp Arg Asp Ala Ala Glu Gly Gly Pro Ser Pro Pro
            100                 105                 110

Ala Ala Arg Gln Asp Ala Ala Arg Pro Pro Ser Met Asn Gly Met Pro
            115                 120                 125

Val Asn Gly Glu Asn Lys Ser Thr Gly Gly Gly Ala Thr Lys Asp
130                 135                 140

Ser Gly Leu Pro Thr Pro Ala Arg Ala Pro His Pro Ser Thr Gln Asn
145                 150                 155                 160

Arg Ala Pro Val Asn Gly Glu Asn Lys Ala Asn Val Ala Ser Pro Pro
            165                 170                 175

Thr Ser Ile Ala Glu Ala Ala Ala Ser Asp Ser Ala Thr Ile Ser
            180                 185                 190

Ile Ser Asp Lys Ala Pro Glu Ser Val Val Pro Ala Glu Lys Thr Pro
            195                 200                 205

Pro Ser Ser Gly Ser Asn Phe Glu Ser Ser Ala Ser Ala Pro Gly Ser
            210                 215                 220

Asp Thr Val Ser Asp Val Glu Gln Glu Leu Lys Lys Gly Ala Val Val
225                 230                 235                 240

Val Glu Glu Ala Pro Lys Pro Lys Ala Leu Ser Pro Pro Ala Ala Pro
            245                 250                 255

Ala Val Gln Glu Asp Leu Trp Asp Phe Lys Lys Tyr Ile Gly Phe Glu
            260                 265                 270

Glu Pro Val Glu Ala Lys Asp Asp Gly Arg Ala Val Ala Asp Asp Ala
            275                 280                 285

Gly Ser Phe Glu His His Gln Asn His Asp Ser Gly Pro Leu Ala Gly
            290                 295                 300

Glu Asn Val Met Asn Val Val Val Ala Ala Glu Cys Ser Pro Trp
305                 310                 315                 320
```

-continued

```
Cys Lys Thr Gly Gly Leu Gly Asp Val Ala Gly Ala Leu Pro Lys Ala
            325                 330                 335
Leu Ala Lys Arg Gly His Arg Val Met Val Val Pro Arg Tyr Gly
        340                 345                 350
Asp Tyr Glu Ala Tyr Asp Val Gly Val Arg Lys Tyr Tyr Lys Ala
        355                 360                 365
Ala Gly Gln Asp Met Glu Val Asn Tyr Phe His Ala Tyr Ile Asp Gly
        370                 375                 380
Val Asp Phe Val Phe Ile Asp Ala Pro Leu Phe Arg His Arg Gln Glu
385                 390                 395                 400
Asp Ile Tyr Gly Gly Ser Arg Gln Glu Ile Met Lys Arg Met Ile Leu
                405                 410                 415
Phe Cys Lys Ala Ala Val Glu Val Pro Trp His Val Pro Cys Gly Gly
            420                 425                 430
Val Pro Tyr Gly Asp Gly Asn Leu Val Phe Ile Ala Asn Asp Trp His
                435                 440                 445
Thr Ala Leu Leu Pro Val Tyr Leu Lys Ala Tyr Tyr Arg Asp His Gly
        450                 455                 460
Leu Met Gln Tyr Thr Arg Ser Ile Met Val Ile His Asn Ile Ala His
465                 470                 475                 480
Gln Gly Arg Gly Pro Val Asp Glu Phe Pro Phe Thr Glu Leu Pro Glu
                485                 490                 495
His Tyr Leu Glu His Phe Arg Leu Tyr Asp Pro Val Gly Gly Glu His
            500                 505                 510
Ala Asn Tyr Phe Ala Ala Gly Leu Lys Met Ala Asp Gln Val Val Val
                515                 520                 525
Val Ser Pro Gly Tyr Leu Trp Glu Leu Lys Thr Val Glu Gly Gly Trp
        530                 535                 540
Gly Leu His Asp Ile Ile Arg Gln Asn Asp Trp Lys Thr Arg Gly Ile
545                 550                 555                 560
Val Asn Gly Ile Asp Asn Met Glu Trp Asn Pro Glu Val Asp Ala His
                565                 570                 575
Leu Lys Ser Asp Gly Tyr Thr Asn Phe Ser Leu Arg Thr Leu Asp Ser
            580                 585                 590
Gly Lys Arg Gln Cys Lys Glu Ala Leu Gln Arg Glu Leu Gly Leu Gln
        595                 600                 605
Val Arg Ala Asp Val Pro Leu Leu Gly Phe Ile Gly Arg Leu Asp Gly
        610                 615                 620
Gln Lys Gly Val Glu Ile Ile Ala Asp Ala Met Pro Trp Ile Val Ser
625                 630                 635                 640
Gln Asp Val Gln Leu Val Met Leu Gly Thr Gly Arg His Asp Leu Glu
                645                 650                 655
Ser Met Leu Gln His Phe Glu Arg Glu His His Asp Lys Val Arg Gly
            660                 665                 670
Trp Val Gly Phe Ser Val Arg Leu Ala His Arg Ile Thr Ala Gly Ala
                675                 680                 685
Asp Ala Leu Leu Met Pro Ser Arg Phe Glu Pro Cys Gly Leu Asn Gln
        690                 695                 700
Leu Tyr Ala Met Ala Tyr Gly Thr Val Pro Val His Ala Val Gly
705                 710                 715                 720
Gly Leu Arg Asp Thr Val Pro Pro Phe Asp Pro Phe Asn His Ser Gly
                725                 730                 735
Leu Gly Trp Thr Phe Asp Arg Ala Glu Ala His Lys Leu Ile Glu Ala
```

```
                    740                 745                 750
Leu Gly His Cys Leu Arg Thr Tyr Arg Asp Phe Lys Glu Ser Trp Arg
            755                 760                 765

Ala Leu Gln Glu Arg Gly Met Ser Gln Asp Phe Ser Trp Glu His Ala
    770                 775                 780

Ala Lys Leu Tyr Glu Asp Val Leu Val Lys Ala Lys Tyr Gln Trp
785                 790                 795
```

```
<210> SEQ ID NO 3
<211> LENGTH: 20
<212> TYPE: DNA
<213> ORGANISM: Artificial sequence
<220> FEATURE:
<223> OTHER INFORMATION: Oligonucleotide

<400> SEQUENCE: 3
gaagaagctc caaagccaaa                                              20

<210> SEQ ID NO 4
<211> LENGTH: 20
<212> TYPE: DNA
<213> ORGANISM: Artificial sequence
<220> FEATURE:
<223> OTHER INFORMATION: Oligonucleotide

<400> SEQUENCE: 4
ggctcctcga aaccaatgta                                              20

<210> SEQ ID NO 5
<211> LENGTH: 27
<212> TYPE: DNA
<213> ORGANISM: Artificial sequence
<220> FEATURE:
<223> OTHER INFORMATION: Oligonucleotide

<400> SEQUENCE: 5
tcttgaaatc ccaaaggtct tcttgta                                      27

<210> SEQ ID NO 6
<211> LENGTH: 20
<212> TYPE: DNA
<213> ORGANISM: Artificial sequence
<220> FEATURE:
<223> OTHER INFORMATION: Oligonucleotide

<400> SEQUENCE: 6
gtcatcagct cgcgttgact                                              20

<210> SEQ ID NO 7
<211> LENGTH: 19
<212> TYPE: DNA
<213> ORGANISM: Artificial sequence
<220> FEATURE:
<223> OTHER INFORMATION: Oligonucleotide

<400> SEQUENCE: 7
tcaatcggta ggagcgacg                                               19

<210> SEQ ID NO 8
<211> LENGTH: 26
<212> TYPE: DNA
<213> ORGANISM: Artificial sequence
<220> FEATURE:
<223> OTHER INFORMATION: Oligonucleotide
```

```
<400> SEQUENCE: 8
acgtccctgc cctttgtaca caccgc                                          26
```